(12) United States Patent
Gong et al.

(10) Patent No.: US 8,536,172 B2
(45) Date of Patent: Sep. 17, 2013

(54) INHIBITORS OF JNK

(75) Inventors: Leyi Gong, San Mateo, CA (US);
Xiaochun Han, Cedar Grove, NJ (US);
Ferenc Makra, Palo Alto, CA (US);
Wylie Solang Palmer, Morristown, NJ (US); Lubica Raptova, Sunnyvale, CA (US)

(73) Assignee: Roche Palo Alto LLC, San Francisco, CA (US)

( * ) Notice: Subject to any disclaimer, the term of this patent is extended or adjusted under 35 U.S.C. 154(b) by 400 days.

(21) Appl. No.: 12/852,540

(22) Filed: Aug. 9, 2010

(65) Prior Publication Data

US 2011/0034470 A1    Feb. 10, 2011

Related U.S. Application Data

(60) Provisional application No. 61/232,522, filed on Aug. 10, 2009.

(51) Int. Cl.
*A61K 31/495* (2006.01)

(52) U.S. Cl.
USPC ........................ 514/249; 514/252.19; 514/275

(58) Field of Classification Search
USPC .................... 514/249, 252.19, 275; 544/295, 544/324
See application file for complete search history.

(56) References Cited

U.S. PATENT DOCUMENTS

2008/0146565 A1*   6/2008  Dunn et al. ................ 514/234.5

FOREIGN PATENT DOCUMENTS

WO   2008/028860   3/2008

OTHER PUBLICATIONS

International Search Report, application No. PCT/EP2010/061476, dated Sep. 21, 2010.

* cited by examiner

*Primary Examiner* — Andrew D Kosar
*Assistant Examiner* — John S Kenyon

(57) ABSTRACT

The invention relates to JNK inhibitors and corresponding methods, formulations, and compositions for inhibiting JNK and treating JNK-mediated disorders. The application discloses JNK inhibitors, as described below in Formula I:

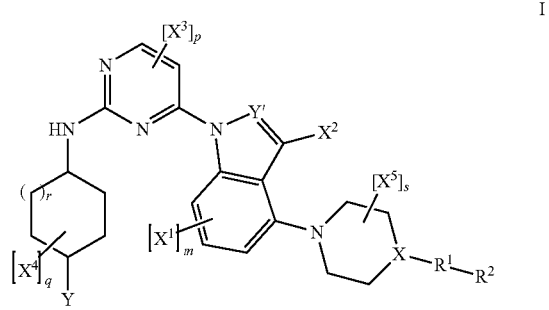

wherein p, q, Y', r, $R^1$, $R^2$, X, $X^1$, $X^2$, $X^3$, and $X^4$ are as defined herein. The compounds and compositions disclosed herein are useful to modulate the activity of JNK and treat diseases associated with JNK activity. Disclosed are methods and formulations for inhibiting JNK and treating JNK-mediated disorders, and the like, with the compounds, and processes for making said compounds, and corresponding compositions, disclosed herein.

14 Claims, No Drawings

INHIBITORS OF JNK

CROSS-REFERENCE TO RELATED APPLICATIONS

This application is entitled to the benefit of U.S. provisional patent application Ser. No. 61/232,522 filed on Aug. 10, 2009, the disclosure of which is incorporated herein by reference.

FIELD OF THE INVENTION

This invention relates generally to the fields of medicinal chemistry and treatment of inflammatory disorders. More particularly, the invention relates to JNK inhibitors, processes for making said inhibitors, and corresponding methods, formulations, and compositions for inhibiting JNK and treating JNK-mediated disorders, and the like.

BACKGROUND OF THE INVENTION

JNK The c-Jun N-terminal kinases (JNKs) are members of mitogen-activated protein kinase family along with p38 and extracellular signal-regulated kinases (ERKs). Three distinct genes (jnk1, jnk2 and jnk3) encoding 10 splice variants have been identified. JNK1 and JNK2 are expressed in a wide variety of tissues, whereas JNK3 is mainly expressed in neurons, and to a lesser extent in heart and testes. Members of JNK family are activated by pro-inflammatory cytokines such as tumor necrosis factor α (TNF-α) and interleukin-1β (IL-1β), as well as environmental stresses. The activation of JNKs is mediated by its upstream kinases, MKK4 and MKK7, via dual phosphorylation of Thr-183 and Tyr-185. It has been shown that MKK4 and MKK7 can be activated by the diverse upstream kinases, including MEKK1 and MEKK4, depending upon the external stimuli and cellular context. The specificity of JNK signaling is achieved by forming a JNK-specific signaling complex containing multiple components of the kinase cascade by use of scaffold proteins called JNK-interacting proteins. JNKs have been shown to play important roles in inflammation, T cell functions, apoptosis and cellular survival by phosphorylating specific substrates, including transcription factors such as c-Jun, the component of activator protein-1 (AP1) family, and ATF2, as well as non-transcription factors such as IRS-1 and Bcl-2. Over-activation of JNK is believed to be an important mechanism in autoimmune, inflammatory, metabolic, neurological diseases as well as cancer.

Rheumatoid arthritis (RA) is a systemic autoimmune disease characterized by chronic inflammation of the joints. In addition to the joint swelling and pain caused by the inflammatory process, most RA patients ultimately develop debilitating joint damage and deformation. Several lines of compelling pharmacological and genetic evidence in cellular and animal models strongly suggest the relevance and importance of the activated JNK in the pathogenesis of RA. First, abnormal activation of JNK was detected in both human arthritic joints from RA patients and rodent arthritic joints from animal models of arthritis. In addition, inhibition of JNK activation by selective JNK inhibitors blocked proinflammatory cytokines and MMP production in human synoviocytes, macrophages and lymphocytes. Importantly, administration of the selective JNK inhibitors in rats with adjuvant arthritis or in mice with collagen-induced arthritis effectively protected joints from destruction and significantly reduced paw swelling by inhibiting cytokine and collagenase expression.

Asthma is a chronic inflammatory disease of airways, characterized by the presence of a cellular inflammatory process and by bronchial hyper-responsiveness associated with structural changes of the airways. This disorder has been shown to be driven by many cell types in the airways, including T lymphocytes, eosinophils, mast cells, neutrophils and epithelial cells. JNKs have emerged as promising therapeutic targets for asthma based upon the recent proof-of-concept studies: it has been shown that JNK inhibitors significantly blocked RANTES production in activated human airway smooth cells. More importantly, the JNK inhibitors showed good efficacy in chronic rat and mouse models for their abilities to reduce cellular infiltration, inflammation, hyper-responsiveness, smooth muscle proliferation, and IgE production. These observations suggest important roles of JNKs in the allergic inflammation, airway remodeling process associated with hyper-responsiveness. Therefore, blockade of JNK activity is expected to be beneficial for the treatment of asthma.

Type 2 diabetes is the most serious and prevalent metabolic disease characterized by insulin resistance and insulin secretion impairment as a result of chronic low-level inflammation and abnormal lipid metabolism associated with oxidative stress. It has been reported that JNK activity is abnormally elevated in various diabetic target tissues under obese and diabetic conditions. Activation of the JNK pathway by pro-inflammatory cytokines and oxidative stresses negatively regulates insulin signaling via phosphorylation of insulin receptor substrate-1 (IRS-1) at $Ser^{307}$, therefore contributes to insulin resistance and glucose tolerance. Compelling genetic evidence came from elegant animal model studies using $jnk^{-/-}$ mice crossed with either genetic (ob/ob) obese mice or dietary obese mice. Loss of JNK1 ($JNK1^{-/-}$), but not JNK2 functions ($jnk2^{-/-}$), protected obese mice from body gains, increased steady-state levels of blood glucose, and decreased plasma insulin levels. These studies demonstrated the potential utility of JNK inhibitor in the treatment of obesity/type 2 diabetes.

Neurodegenerative diseases, such as Alzheimer's (AD), Parkinson's (PD) and stroke are CNS diseases characterized by synaptic loss, neuronal atrophy and death. The JNK pathway leading to c-Jun activation has been shown to play a causal role in apoptosis of isolated primary embryonic neurons and multiple neuronal cell lines upon induction of a variety of stimuli. Over-activation of JNK was observed in human brains from AD patients or rodent brain sections derived from animal models of neurodegenerative diseases. For example, increased phospho-JNKs were detected in the post-mortem brains from the AD patients. Administration of JNK inhibitory peptide (JIP-1 peptide) in the rodent model of AD induced by β-amyloid peptide administration prevented the impairment of synaptic plasticity. In the animal models of PD (MPTP model), elevated phospho-MKK4 and phospho-JNKs were observed concomitantly with the neuronal cell death. Adenoviral gene transfer of JNK inhibitory peptide (JIP-1 peptide) into striatum of mice attenuated behavioral impairment by inhibiting MPTP-mediated JNK, c-Jun and caspase activation, therefore blocking neuronal cell death in the substantia nigra. In addition, in the animal model of ischemic stroke induced by glutamate excitotoxicity, mice deficient in JNK3, but not JNK1 or JNK2, were resistant to kainic acid (glutamate receptor agonist)-mediated seizure or neuronal death. These data suggest JNK3 was mainly responsible for glutamate excitotoxicity, an important component in ischemic conditions. Taken together, data has emerged suggesting JNKs as attractive target for multiple CNS diseases associated with neuronal cell death.

Uncontrolled cellular growth, proliferation and migration along with de-regulated angiogenesis lead to the formation of malignant tumors. The JNK signal transduction pathway may not act exclusively in apoptosis, sustained JNK activation leading to AP1 activation has recently been implicated to contribute to the cellular survival of specific cancer types such as glial tumors and BCL-ABL transformed B lymphoblasts. In the case of glial tumors, enhanced JNK/AP1 activity was seen in most of the primary brain tumor samples. For the transformed B lymphoblasts, BCL-ABL was shown to activate the JNK pathway which in turn up-regulated expression of anti-apoptotic bcl-2 gene. Interestingly, the multi-drug resistance and hyper-proliferation seen in treatment-refractory AML (acute myeloid leukemia) patients has been causally linked to the sustained JNK activity present in these AML samples. Activation of JNK in leukemic cells resulted in induced expression of efflux pumps such as mdr1 and MRP1 responsible for multidrug resistance. Also, genes with a survival benefit in response to oxidative stress including glutathione-S-transferase π and γ-glutamyl cysteine synthase were also upregulated by the activated JNK pathway.

Kidney diseases are characterized by loss of nephron function caused by progressive glomerulosclerosis and tubulointerstitial fibrosis. Renal disease may develop as a consequence of many conditions including inflammation, hypertension, diabetes, or acute tissue damage caused by antibiotics, contrast agents, or other nephrotoxic substances. JNK signaling has been shown to be upregulated in pathology specimens from many human renal diseases, including immune and non-immune mediated glomerulonephritis, diabetic nephropathy, hypertension, acute injury (1), and appears to play a signaling role in polycystic kidney disease (2). Compelling evidence for a central role of JNK and the therapeutic potential of JNK inhibitors is supported by studies in animal models of renal injury. JNK was increased in a rat anti-glomerular basement membrane induced glomerulonephritis model and renal function was improved by a specific inhibitor in both acute and chronic disease paradigms (3). JNK was also increased in the Dahl salt-sensitive hypertensive rat, a model of hypertensive renal disease (4), as well as in models of renal ischemia-reperfusion injury (5,6). The cellular mechanisms by which JNK may contribute to renal injury are, in part, by up-regulation of pro-inflammatory mediators in macrophages, as well as by activation of pro-fibrotic, and pro-apoptotic pathways directly in cells of the renal glomerulus and the tubular epithelium (7). The ability to improve renal function by inhibition of JNK in multiple disease models, suggests JNKs as attractive targets for therapy of renal diseases of various etiology.

SUMMARY OF THE INVENTION

In one aspect, the application provides a compound of formula I

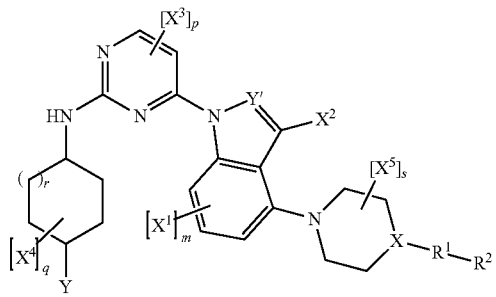

or a pharmaceutically acceptable salt thereof, wherein:

Y' is CH or N;

X is CH or N;

each $X^1$ is independently halogen, lower alkyl, lower alkoxy, lower haloalkyl, or hydroxy;

m is 0, 1, or 2;

$X^2$ is H, lower alkyl, lower alkoxy, amido, lower haloalkyl, or lower haloalkoxy;

$X^3$ is lower alkyl, lower alkoxy, or lower haloalkyl;

p is 0 or 1;

each $X^4$ is independently lower alkyl, lower alkoxy, lower haloalkyl, hydroxy, lower hydroxylalkyl, $OC(=O)Z^2$, or halogen;

$X^5$ is lower alkyl;

s is 0, 1, or 2;

q is 0, 1, or 2;

r is 0 or 1;

Y is H, OH, $C(=O)Z^2$, $C(=O)OZ^2$, $OZ^2$, $OC(=O)Z^2$, $N(Z^1)C(=O)(Z^2)$, $C(Z^1)_2S(O)_2Z^2$, $N(Z^1)S(O)_2Z^2$, $N(Z^1)S(O)_2N(Z^1)(Z^2)$, $C(Z^1)_2(Z^2)$, or $(C=O)N(Z^1)(Z^2)$;

$Z^1$ is H or $Z^{1'}$;

$Z^{1'}$ is lower alkyl, optionally substituted with one or more $Z^{1''}$;

each $Z^{1''}$ is independently halogen, hydroxy, lower haloalkyl, dialkylamino or amino;

$Z^2$ is H or $Z^{2'}$;

$Z^{2'}$ is hydroxy, lower alkyl, lower alkoxy, lower hydroxyalkyl, lower haloalkyl, cycloalkyl, cycloalkyl lower alkyl, heterocycloalkyl, heterocycloalkyl lower alkyl, optionally substituted with one or more $Z^{2''}$;

each $Z^{2''}$ is independently halogen, hydroxy, lower alkyl, cycloalkyl, cyano, lower haloalkyl, amino, carboxylic acid, ester, or lower alkoxy;

$R^1$ is a bond, $C(=O)$, $C(=O)O$, $C(=O)CH_2OC(=O)$, $C(=O)CH_2NHC(=O)O$, or $S(=O)_2$;

$R^2$ is H or $R^{2'}$;

$R^{2'}$ is hydroxy, lower alkyl, $N(R^3)_2$, lower hydroxyalkyl, or lower haloalkyl, optionally substituted with one or more $R^{2''}$;

each $R^{2''}$ is independently cyano, amino, dialkylamino, hydroxy, lower hydroxyalkyl, or lower alkoxy; and each $R^3$ is independently H, lower alkyl, lower cycloalkyl, phenyl, lower heterocycloalkyl, or both $R^3$ together form a heterocyclic ring;

with the proviso that when X is N, $X^2$ is H, Y' is CH, $R^1$ is $C(=O)$, $R^2$ is methyl, r is 1, m is 0, p is 0, q is 0, Y is $N(Z^1)S(O)_2Z^2$, and $Z^2$ is methyl, then $Z^1$ is not H or hydroxyethyl.

In one aspect, the application provides a method of treating a JNK-mediated disorder in a subject having a JNK-mediated disorder, said method comprising administering to a subject in need thereof a therapeutically effective amount of any of the above compounds.

In one aspect, the application provides a pharmaceutical composition comprising the compound of any one of the above embodiments, admixed with at least one pharmaceutically acceptable carrier, excipient or diluent.

DETAILED DESCRIPTION OF THE INVENTION

In one aspect, the application provides a compound of formula I

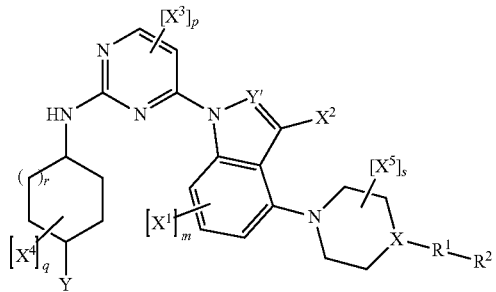

or a pharmaceutically acceptable salt thereof,
wherein:
Y' is CH or N;
X is CH or N;
each $X^1$ is independently halogen, lower alkyl, lower alkoxy, lower haloalkyl, or hydroxy;
m is 0, 1, or 2;
$X^2$ is H, lower alkyl, lower alkoxy, amido, lower haloalkyl, or lower haloalkoxy;
$X^3$ is lower alkyl, lower alkoxy, or lower haloalkyl;
p is 0 or 1;
each $X^4$ is independently lower alkyl, lower alkoxy, lower haloalkyl, hydroxy, lower hydroxyalkyl, $OC(=O)Z^2$, or halogen;
$X^5$ is lower alkyl;
s is 0, 1, or 2;
q is 0, 1, or 2;
r is 0 or 1;
Y is H, OH, $C(=O)Z^2$, $C(=O)OZ^2$, $OZ^2$, $OC(=O)Z^2$, $N(Z^1)C(=O)(Z^2)$, $C(Z^1)_2S(O)_2Z^2$, $N(Z^1)S(O)_2Z^2$, $N(Z^1)S(O)_2N(Z^1)(Z^2)$, $C(Z^1)_2(Z^2)$, or $(C=O)N(Z^1)(Z^2)$;
$Z^1$ is H or $Z^{1'}$;
  $Z^{1'}$ is lower alkyl, optionally substituted with one or more $Z^{1''}$;
    each $Z^{1''}$ is independently halogen, hydroxy, lower haloalkyl, dialkylamino or amino;
$Z^2$ is H or $Z^{2'}$;
  $Z^{2'}$ is hydroxy, lower alkyl, lower alkoxy, lower hydroxyalkyl, lower haloalkyl, cycloalkyl, cycloalkyl lower alkyl, heterocycloalkyl, heterocycloalkyl lower alkyl, optionally substituted with one or more $Z^{2''}$;
    each $Z^{2''}$ is independently halogen, hydroxy, lower alkyl, cycloalkyl, cyano, lower haloalkyl, amino, carboxylic acid, ester, or lower alkoxy;
$R^1$ is a bond, $C(=O)$, $C(=O)O$, $C(=O)CH_2C(=O)$, $C(=O)CH_2NHC(=O)O$, or $S(=O)_2$;
$R^2$ is H or $R^{2'}$;
  $R^{2'}$ is hydroxy, lower alkyl, $N(R^3)_2$, lower hydroxyalkyl, or lower haloalkyl, optionally substituted with one or more $R^{2''}$;
    each $R^{2''}$ is independently cyano, amino, dialkylamino, hydroxy, lower hydroxyalkyl, or lower alkoxy; and each $R^3$ is independently H, lower alkyl, lower cycloalkyl, phenyl, lower heterocycloalkyl, or both $R^3$ together form a heterocyclic ring;
with the proviso that when X is N, $X^2$ is H, Y' is CH, $R^1$ is $C(=O)$, $R^2$ is methyl, r is 1, m is 0, p is 0, q is 0, Y is $N(Z^1)S(O)_2Z^2$, and $Z^2$ is methyl, then $Z^1$ is not H or hydroxyethyl.

In one variation of formula I, m is 0, $X^2$ is H, p is 0, q is 0, r is 0, X is N, Y' is CH, $R^1$ is $C(=O)$, $R^2$ is $R^{2'}$, $R^{2'}$ is methylene, and $R^{2''}$ is cyano.

In one variation of formula I, m is 0, p is 0, q is 0, r is 1, X is N, Y' is CH, $R^1$ is $C(=O)$, $R^2$ is $R^{2'}$, $R^{2'}$ is methylene, and $R^{2''}$ is cyano.

In one variation of formula I, m is 0, $X^2$ is H, p is 0, q is 0, r is 1, X is N, Y' is CH, $R^1$ is $C(=O)$, $R^2$ is $R^{2'}$, and $R^{2'}$ is methyl.

In one variation of formula I, m is 0, p is 0, q is 0, r is 1, X is CH, Y' is CH, $R^1$ is $S(=O)_2$, $R^2$ is $R^{2'}$, and $R^{2'}$ is methyl.

In one variation of formula I, $R^1$ is $C(=O)$, $R^2$ is $R^{2'}$, $R^{2'}$ is methylene, and $R^{2''}$ is cyano.

In one variation of formula I, $R^1$ is $S(=O)_2$, $R^2$ is $R^{2'}$, and $R^{2'}$ is methyl.

The application provides the compounds of Formula I selected from the group consisting of:
N-{4-[4-(4-Piperazin-1-yl-indol-1-yl)-pyrimidin-2-ylamino]-cyclohexyl}-methanesulfonamide;
4-[4-(4-Piperidin-1-yl-indol-1-yl)-pyrimidin-2-ylamino]-cyclohexanol;
N-(4-{4-[4-(4-Methanesulfonyl-piperazin-1-yl)-indol-1-yl]-pyrimidin-2-ylamino}-cyclohexyl)-methanesulfonamide;
N-(4-{4-[4-(4-Hydroxy-piperidin-1-yl)-indol-1-yl]-pyrimidin-2-ylamino}-cyclohexyl)-methanesulfonamide;
N-(4-{4-[4-(4-Acetyl-piperazin-1-yl)-indol-1-yl]-pyrimidin-2-ylamino}-cyclohexyl)-N-meth) methanesulfonamide;
N-(4-{4-[4-(4-Methanesulfonyl-piperidin-1-yl)-indol-1-yl]-pyrimidin-2-ylamino}-cyclohexyl methanesulfonamide;
4-{1-[2-(4-Methanesulfonylamino-cyclohexylamino)-pyrimidin-4-yl]-1H-indol-4-yl}-piperazine-1-carboxylic acid amide;
4-{1-[2-(4-Methanesulfonylamino-cyclohexylamino)-pyrimidin-4-yl]-1H-indol-4-yl}-piperazine-1-sulfonic acid amide;
N-[4-(4-{4-[4-(2-Cyano-acetyl)-piperazin-1-yl]-indol-1-yl}-pyrimidin-2-ylamino)-cyclohexyl]-methanesulfonamide;
Acetic acid 2-(4-{1-[2-(4-methanesulfonylamino-cyclohexylamino)-pyrimidin-4-yl]-1H-indol-4-yl}-piperazin-1-yl)-2-oxo-ethyl ester;
N-[4-(4-{4-[4-(2-Hydroxy-acetyl)-piperazin-1-yl]-indol-1-yl}-pyrimidin-2-ylamino)-cyclohexyl]-methanesulfonamide;
4-{4-[4-(4-Methanesulfonyl-piperidin-1-yl)-indol-1-yl]-pyrimidin-2-ylamino}-cyclohexanol;
N-(4-{4-[4-(4-Methanesulfonyl-piperidin-1-yl)-indol-1-yl]-pyrimidin-2-ylamino}-cyclohexyl)-acetamide;
2-(4-{4-[4-(4-Methanesulfonyl-piperidin-1-yl)-indol-1-yl]-pyrimidin-2-ylamino}-cyclohexyl)-propan-2-ol;
[4-{4-[4-(4-Methanesulfonyl-piperidin-1-yl)-indol-1-yl]-pyrimidin-2-ylamino}-cyclohexyl]aminodimethylsulfonamide;
4-{4-[4-(4-Methanesulfonyl-piperidin-1-yl)-indol-1-yl]-pyrimidin-2-ylamino}-1-methyl-cyclohexanol;
4-{4-[4-(4-Methanesulfonyl-piperidin-1-yl)-indol-1-yl]-pyrimidin-2-ylamino}-1-methyl-cyclohexanol;

(4-Hydroxy-piperidin-1-yl)-(4-{4-[4-(4-methanesulfonyl-piperidin-1-yl)-indol-1-yl]-pyrimidin-2-ylamino}-cyclohexyl)-methanone;

4-{4-[4-(4-Methanesulfonyl-piperidin-1-yl)-indol-1-yl]-pyrimidin-2-ylamino}-cyclohexanecarboxylic acid ethylamide;

4-{4-[4-(4-Methanesulfonyl-piperidin-1-yl)-indol-1-yl]-pyrimidin-2-ylamino}-cyclohexanecarboxylic acid ethyl ester;

1-[(R)-4-(1-{2-[4-(4-Hydroxy-piperidine-1-carbonyl)-cyclohexylamino]-pyrimidin-4-yl}-1H-indol-4-yl)-3-methyl-piperazin-1-yl]-ethanone;

[2-(4-{1-[2-(4-Methanesulfonylamino-cyclohexylamino)-pyrimidin-4-yl]-1H-indol-4-yl}-piperazin-1-yl)-2-oxo-ethyl]-carbamic acid tert-butyl ester;

N-[4-(4-{4-[4-(2-Dimethylamino-acetyl)-piperazin-1-yl]-indol-1-yl}-pyrimidin-2-ylamino)-cyclohexyl]-methanesulfonamide;

N-[4-(4-{4-[4-(2-Amino-acetyl)-piperazin-1-yl]-indol-1-yl}-pyrimidin-2-ylamino)-cyclohexyl]-methanesulfonamide;

3-[4-(1-{2-[4-((R)-3-Hydroxy-pyrrolidin-1-ylmethyl)-cyclohexylamino]-pyrimidin-4-yl}-1H-indol-4-yl)-piperazin-1-yl]-3-oxo-propionitrile;

N-[4-(4-{4-[4-(2-Cyano-acetyl)-piperazin-1-yl]-indol-1-yl}-pyrimidin-2-ylamino)-cyclohexyl]-N-(2-dimethylamino-ethyl)-methanesulfonamide;

3-(4-{1-[2-(4-Hydroxymethyl-cyclohexylamino)-pyrimidin-4-yl]-1H-indol-4-yl}-piperazin-1-yl)-3-oxo-propionitrile;

3-[4-(1-{2-[4-((S)-3-Hydroxy-pyrrolidin-1-ylmethyl)-cyclohexylamino]-pyrimidin-4-yl}-1H-indol-4-yl)-piperazin-1-yl]-3-oxo-propionitrile;

1-[4-(1-{2-[4-((R)-3-Hydroxy-pyrrolidin-1-ylmethyl)-cyclohexylamino]-pyrimidin-4-yl}-1H-indol-4-yl)-piperazin-1-yl]-ethanone;

(4-Ethoxy-piperidin-1-yl)-(4-{4-[4-(4-methanesulfonyl-piperidin-1-yl)-indol-1-yl]-pyrimidin-2-ylamino}-cyclohexyl)-methanone;

((R)-3-Ethoxy-pyrrolidin-1-yl)-(4-{4-[4-(4-methanesulfonyl-piperidin-1-yl)-indol-1-yl]-pyrimidin-2-ylamino}-cyclohexyl)-methanone;

((S)-3-Ethoxy-pyrrolidin-1-yl)-(4-{4-[4-(4-methanesulfonyl-piperidin-1-yl)-indol-1-yl]-pyrimidin-2-ylamino}-cyclohexyl)-methanone;

Cyano-acetic acid (1R,3S)-3-(4-{4-[4-(2-cyano-acetyl)-piperazin-1-yl]-indol-1-yl}-pyrimidin-2-ylamino)-cyclohexyl ester;

3-(4-{1-[2-((1S,3S)-3-Hydroxy-cyclohexylamino)-pyrimidin-4-yl]-1H-indol-4-yl}-piperazin-1-yl)-3-oxo-propionitrile;

3-(4-{1-[2-((1S,3R)-3-Hydroxy-cyclohexylamino)-pyrimidin-4-yl]-1H-indol-4-yl}-piperazin-1-yl)-3-oxo-propionitrile;

Cyano-acetic acid (1S,3S)-3-(4-{4-[4-(2-cyano-acetyl)-piperazin-1-yl]-indol-1-yl}-pyrimidin-2-ylamino)-cyclohexyl ester;

1-{4-[1-(2-Cyclohexylamino-pyrimidin-4-yl)-1H-indol-4-yl]-piperazin-1-yl}-ethanone;

3-{4-[1-(2-Cyclohexylamino-pyrimidin-4-yl)-1H-indol-4-yl]-piperazin-1-yl}-3-oxo-propionitrile;

1-[4-(1-{2-[4-(2-Methoxy-ethoxy)-cyclohexylamino]-pyrimidin-4-yl}-1H-indol-4-yl)-piperazin-1-yl]-ethanone;

3-[4-(1-{2-[4-(2-Methoxy-ethoxy)-cyclohexylamino]-pyrimidin-4-yl}-1H-indol-4-yl)-piperazin-1-yl]-3-oxo-propionitrile;

1-(4-{1-[2-(4-Methanesulfonylmethyl-cyclohexylamino)-pyrimidin-4-yl]-1H-indol-4-yl}-piperazin-1-yl)-ethanone;

3-(4-{1-[2-(4-Methanesulfonylmethyl-cyclohexylamino)-pyrimidin-4-yl]-1H-indol-4-yl}-piperazin-1-yl)-3-oxo-propionitrile;

1-[4-(1-{2-[4-(1-Hydroxy-1-methyl-ethyl)-cyclohexylamino]-pyrimidin-4-yl}-1H-indol-4-yl)-piperazin-1-yl]-ethanone;

N-[4-(4-{4-[4-(2-Cyano-acetyl)-piperazin-1-yl]-indol-1-yl}-pyrimidin-2-ylamino)-cyclohexyl]-N-(2-hydroxy-ethyl)-methanesulfonamide;

3-[4-(1-{2-[4-(1-Hydroxy-1-methyl-ethyl)-cyclohexylamino]-pyrimidin-4-yl}-1H-indol-4-yl)-piperazin-1-yl]-3-oxo-propionitrile;

(4-Ethyl-piperazin-1-yl)-(4-{4-[4-(4-methanesulfonyl-piperidin-1-yl)-indol-1-yl]-pyrimidin-2-ylamino}-cyclohexyl)-methanone;

(4-Cyclopropyl-piperazin-1-yl)-(4-{4-[4-(4-methanesulfonyl-piperidin-1-yl)-indol-1-yl]-pyrimidin-2-ylamino}-cyclohexyl)-methanone;

(4-tert-Butyl-piperazin-1-yl)-(4-{4-[4-(4-methanesulfonyl-piperidin-1-yl)-indol-1-yl]-pyrimidin-2-ylamino}-cyclohexyl)-methanone;

(4-Cyclobutyl-piperazin-1-yl)-(4-{4-[4-(4-methanesulfonyl-piperidin-1-yl)-indol-1-yl]-pyrimidin-2-ylamino}-cyclohexyl)-methanone;

(4-{4-[4-(4-Methanesulfonyl-piperidin-1-yl)-indol-1-yl]-pyrimidin-2-ylamino}-cyclohexyl)-(octahydro-pyrido[1,2-α]pyrazin-2-yl)-methanone;

(4-{4-[4-(4-Methanesulfonyl-piperidin-1-yl)-indol-1-yl]-pyrimidin-2-ylamino}-cyclohexyl)-(3-trifluoromethyl-5,6-dihydro-8H-[1,2,4]triazolo[4,3-α]pyrazin-7-yl)-methanone;

(Hexahydro-pyrrolo[1,2-α]pyrazin-2-yl)-(4-{4-[4-(4-methanesulfonyl-piperidin-1-yl)-indol-1-yl]-pyrimidin-2-ylamino}-cyclohexyl)-methanone;

(5,6-Dihydro-8H-[1,2,4]triazolo[4,3-α]pyrazin-7-yl)-(4-{4-[4-(4-methanesulfonyl-piperidin-1-yl)-indol-1-yl]-pyrimidin-2-ylamino}-cyclohexyl)-methanone;

(5,6-Dihydro-8H-imidazo[1,2-α]pyrazin-7-yl)-(4-{4-[4-(4-methanesulfonyl-piperidin-1-yl)-indol-1-yl]-pyrimidin-2-ylamino}-cyclohexyl)-methanone;

3-(4-{1-[2-(4-Hydroxy-cyclohexylamino)-pyrimidin-4-yl]-1H-indol-4-yl}-piperazin-1-yl)-3-oxo-propionitrile;

3-[4-(1-{2-[4-(4-Ethyl-piperazine-1-carbonyl)-cyclohexylamino]-pyrimidin-4-yl}-1H-indol-4-yl)-piperazin-1-yl]-3-oxo-propionitrile;

3-(4-{1-[2-(4-Hydroxy-cyclohexylamino)-pyrimidin-4-yl]-1H-indol-4-yl}-piperazin-1-yl)-3-oxo-propionitrile;

3-(4-{1-[2-((1S,3R)-3-Hydroxy-cyclopentylamino)-pyrimidin-4-yl]-1H-indol-4-yl}-piperazin-1-yl)-3-oxo-propionitrile;

3-(4-{1-[2-((1R,3S)-3-Hydroxy-cyclopentylamino)-pyrimidin-4-yl]-1H-indol-4-yl}-piperazin-1-yl)-3-oxo-propionitrile;

3-(4-{1-[2-((1S,3S)-3-Hydroxy-cyclopentylamino)-pyrimidin-4-yl]-1H-indol-4-yl}-piperazin-1-yl)-3-oxo-propionitrile;

3-(4-{1-[2-((1R,3R)-3-Hydroxy-cyclopentylamino)-pyrimidin-4-yl]-1H-indol-4-yl}-piperazin-1-yl)-3-oxo-propionitrile;

4-{4-[4-(4-Methanesulfonyl-piperidin-1-yl)-indol-1-yl]-pyrimidin-2-ylamino}-cyclohexanol;

4-(4-Acetyl-piperazin-1-yl)-1-[2-(4-hydroxy-cyclohexylamino)-pyrimidin-4-yl]-1H-indole-3-carboxylic acid amide;

4-(4-Acetyl-piperazin-1-yl)-1-[2-(4-methanesulfonylm-
ethyl-cyclohexylamino)-pyrimidin-4-yl]-1H-indole-3-
carboxylic acid amide;

4-{4-[4-(4-Methanesulfonyl-piperidin-1-yl)-indazol-1-yl]-
pyrimidin-2-ylamino}-cyclohexanecarboxylic acid ethyl
ester; and 4-{4-[4-(4-Methanesulfonyl-piperidin-1-yl)-indazol-1-yl]-
pyrimidin-2-ylamino}-cyclohexanol.

In one aspect, the application provides a method of treating a JNK-mediated disorder in a subject having a JNK-mediated disorder, said method comprising administering to a subject in need thereof a therapeutically effective amount of any of the above compounds.

In certain embodiments of the method of treating a JNK-mediated disorder, the JNK-mediated disorder is characterized by cellular proliferation.

In certain embodiments of the method of treating a JNK-mediated disorder, the JNK-mediated disorder is arthritis.

In certain embodiments of the method of treating a JNK-mediated disorder, the arthritis is rheumatoid arthritis.

In certain embodiments of the method of treating a JNK-mediated disorder, the JNK-mediated disorder is asthma.

In certain embodiments of the method of treating a JNK-mediated disorder, the JNK-mediated disorder is a metabolic disorder.

In certain embodiments of the method of treating a JNK-mediated disorder, the JNK-mediated disorder is diabetes.

In certain embodiments of the method of treating a JNK-mediated disorder, the JNK-mediated disorder is Alzheimer's disease.

In certain embodiments of the method of treating a JNK-mediated disorder, the JNK-mediated disorder is Parkinson's disease.

In certain embodiments of the method of treating a JNK-mediated disorder, the JNK-mediated disorder is ischemic stroke.

In certain embodiments of the method of treating a JNK-mediated disorder, the JNK-mediated disorder is cancer.

In certain embodiments of the method for treating a JNK-mediated disorder, wherein the JNK-mediated disorder is cancer, the cancer is brain cancer.

In certain embodiments of the method for treating a JNK-mediated disorder, wherein the JNK-mediated disorder is cancer, the cancer is leukemia.

In certain embodiments of the method of treating a JNK-mediated disorder, the JNK-mediated disorder is kidney disease.

In one aspect, the application provides a pharmaceutical composition comprising the compound of any one of the above embodiments, admixed with at least one pharmaceutically acceptable carrier, excipient or diluent.

A method for treating arthritis comprising co-administering to a patient in need thereof a therapeutically effective amount of an anti-inflammatory compound in combination with the compound of any of the above embodiments, variations, or aspects.

All publications cited in this disclosure are incorporated herein by reference in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise. Thus, the phrase "'a' or 'an' entity' as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., m, n, p, q, Q, r, $R^1$, $R^2$, $R^3$, $R^4$, X, $X^1$, $X^2$, $X^3$, $X^4$, $X^5$, $Y^1$, $Y^2$, $Z^1$, and $Z^2$) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or " ------ " drawn through a bond each refer to the point of attachment of a functional group or other chemical moiety to the rest of the molecule of which it is a part. Thus, for example:

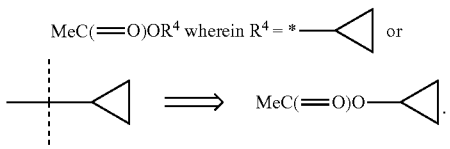

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds of the invention may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbons. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"-, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH (i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxy-phenyl, and the like, including partially hydrogenated derivatives thereof.

The term "base" includes, but is not limited to, NaOH, KOH, LiOH and alkali metal carbonates such as potassium carbonate, sodium carbonate, lithium carbonate, sodium bicarbonate, cesium carbonate and the like.

"Cycloalkyl" or "carbocyclic ring" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Heterocycloalkyl lower alkyl" mean a moiety of the formula -R$^a$-R$^b$, where R$^a$ is lower alkylene and R$^b$ is heterocycloalkyl as defined herein.

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazol, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring; however the point of attachment is on a ring containing a heteroatom.

The term "hydroxyalkyl" as used herein denotes an alkyl radical as herein defined wherein one to three hydrogen atoms on different carbon atoms is/are replaced by hydroxyl groups.

Commonly used abbreviations include: acetyl (Ac), azo-bis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride (BOC₂O), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether (Et₂O), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp), MeSO₂— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), tert-butyldimethylsilyl or t-BuMe₂Si (TBDMS), triethylamine (TEA or Et₃N), 2,2,6,6-tetramethylpiperidine 1-oxyl (TEMPO), triflate or CF₃SO₂— (Tf), trifluoroacetic acid (TFA), 1,1'-bis-2,2,6,6-tetramethylheptane-2,6-dione (TMHD), O-benzotriazol-1-yl-N,N,N', N'-tetramethyluronium tetrafluoroborate (TBTU), thin layer chromatography (TLC), tetrahydrofuran (THF), trimethylsilyl or Me₃Si (TMS), p-toluenesulfonic acid monohydrate (TsOH or pTsOH), 4-Me-C₆H₄SO₂— or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

"Heteroalkyl" means an alkyl moiety as defined herein, including a branched $C_4$-$C_7$ alkyl, wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl; when n is 1, $R^d$ is alkyl, cycloalkyl, or cycloalkylalkyl; and when n is 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-amino-ethyl, 3-aminopropyl, 2-methylsulfonylethyl, aminosulfonylmethyl, aminosulfonylethyl, amino-sulfonylpropyl, methylaminosulfonylmethyl, methylaminosulfonylethyl, methylaminosulfonyl-propyl, and the like.

"Heteroaryl" means a monocyclic or bicyclic moiety of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, thiophenyl, furanyl, pyranyl, pyridinyl, pyrrolyl, pyrazolyl, pyrimidyl, pyridazinyl, quinolinyl, isoquinolinyl, benzofuryl, benzofuranyl, benzothiophenyl, benzothiopyranyl, benz-imidazolyl, benzoxazolyl, benzooxadazolyl, benzothiazolyl, benzothiadiazolyl, benzopyranyl, indolyl, isoindolyl, indazolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

The terms "halo," "halogen," and "halide" are used interchangeably herein and refer to fluoro, chloro, bromo, and iodo.

"Haloalkyl" means alkyl as defined herein in which one or more hydrogen has been replaced with same or different halogen. The term "lower haloalkyl" denotes a straight or branched chain hydrocarbon residue containing 1 to 6 carbon atoms substituted with one or more halogen atom. Exemplary haloalkyls include —$CH_2Cl$, —$CH_2CF_3$, —$CH_2CCl_3$, —$CF_2CF_3$, —$CF_3$, and the like.

"Heterocyclyl", "heterocycle", or "heterocycloalkyl" means a monovalent saturated moiety, consisting of one to two rings, incorporating one, two, or three or four heteroatoms (chosen from nitrogen, oxygen or sulfur). The heterocyclyl ring may be optionally fuse to a heteroaryl group as defined herein. The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydroisoquinolinyl, tetrahydroquinolinyl, tetrahydrisoquinolinyl, octahydro-pyrrolo[1,2-a]pyrazine, octahydro-pyrido[1,2-a]pyrazine, 5,6,7,8-tetrahydro-[1,2,4]triazolo[4,3-a]pyrazine, 5,6,7,8-tetrahydro-imidazo[1,2-a]pyrazine, dihydro-8H-[1,2,4]triazolo[4,3-α]pyrazine, hexahydro-pyrrolo[1,2-α]pyrazine, 5,6-Dihydro-8H-[1,2,4]triazolo[4,3-α]pyrazine, 5,6-Dihydro-8H-imidazo[1,2-α]pyrazine and the like.

"Optionally substituted" means a substituent which is substituted independently with zero to three substituents selected from lower alkyl, halo, OH, cyano, amino, nitro, lower alkoxy, or halo-lower alkyl.

Preferred "oxidizing agents" include peracids like in-chloroperbenzoic acid (MCPBA) and peracetic acid, but other oxidizing agents like hydrogen peroxide, permanganate salts, or persulfate salts can be used to oxidize a thioether to a sulfone.

"Leaving group" means a group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzene-sulfonyloxy, tosyloxy, and thienyloxy, dihalophosphinoyloxy, optionally substituted benzyloxy, isopropyloxy, acyloxy, and the like.

"Optional" or "optionally" means that the subsequently described event or circumstance may but need not occur, and that the description includes instances where the event or circumstance occurs and instances in which it does not.

"Agonist" refers to a compound that enhances the activity of another compound or receptor site.

"Antagonist" refers to a compound that diminishes or prevents the action of another compound or receptor site.

The term "drug candidate" refers to a compound or preparation which is to be tested for possible effect in the treatment of a disease state in an animal, regardless of whether said drug candidate has any known biological activity.

The term "homologous" as used herein refers to a protein that performs substantially the same function in another subject species and shares substantial sequence identity, to the extent that they are recognized in the art as being different versions of the same protein, differing primarily in the species in which they are found. Thus, for example, human ERG, mouse ERG, and rat ERG are all considered homologous to each other.

"Modulator" means a molecule that interacts with a target. The interactions include, but are not limited to, agonist, antagonist, and the like, as defined herein.

"Disease" and "Disease state" means any disease, condition, symptom, disorder or indication.

The term "cell line" refers to a clone of immortalized mammalian cells. A "stable" cell line is a cell line that exhibits substantially consistent characteristics over time (e.g., with each doubling). A stable cell line within the scope of this invention provides a substantial proportion of cells that are capable of providing a seal resistance of greater than about 50 MOhm, a current amplitude of greater than about 200 pA, and provide a current amplitude that does not vary by more than approximately 20% over one hour under control conditions.

"Pharmaceutically acceptable salts" of a compound means salts that are pharmaceutically acceptable, as defined herein, and that possess the desired pharmacological activity of the parent compound. Such salts include:

(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or (2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

It should be understood that all references to pharmaceutically acceptable salts include solvent addition forms (solvates) or crystal forms (polymorphs) as defined herein, of the same acid addition salt.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" includes mammals and birds. "Mammals" means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

"Pharmacological effect" as used herein encompasses effects produced in the subject that achieve the intended purpose of a therapy. For example, a pharmacological effect would be one that results in the prevention, alleviation or reduction of urinary incontinence in a treated subject.

"Disease state" means any disease, condition, symptom, or indication.

"Treating" or "treatment" of a disease state includes (i) preventing the disease state, i.e. causing the clinical symptoms of the disease state not to develop in a subject that may be exposed to or predisposed to the disease state, but does not yet experience or display symptoms of the disease state; (ii) inhibiting the disease state, i.e., arresting the development of the disease state or its clinical symptoms; or (iii) relieving the disease state, i.e., causing temporary or permanent regression of the disease state or its clinical symptoms.

All patents and publications identified herein are incorporated herein by reference in their entirety.

Compounds and Preparation

The compounds described below are JNK inhibitors useful for inhibiting JNK and treating JNK-mediated disorders, and the like. Examples of representative compounds encompassed by the present invention and within the scope of the invention are provided in Table X as compounds.

These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE X

| | Structure | Nomenclature |
|---|---|---|
| I-1 | 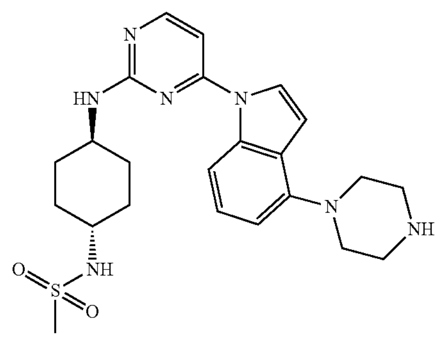 [SMILES: CS(=O)(=O)N[C@H]1CC[C@H](Nc2nccc(-n3ccc4c(N5CCNCC5)cccc43)n2)CC1] | N-{4-[4-(4-Piperazin-1-yl-indol-1-yl)-pyrimidin-2-ylamino]-cyclohexyl}-methanesulfonamide |
| I-2 | 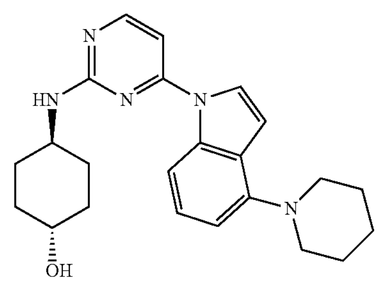 [SMILES: O[C@H]1CC[C@H](Nc2nccc(-n3ccc4c(N5CCCCC5)cccc43)n2)CC1] | 4-[4-(4-Piperidin-1-yl-indol-1-yl)-pyrimidin-2-ylamino]-cyclohexanol |
| I-3 | 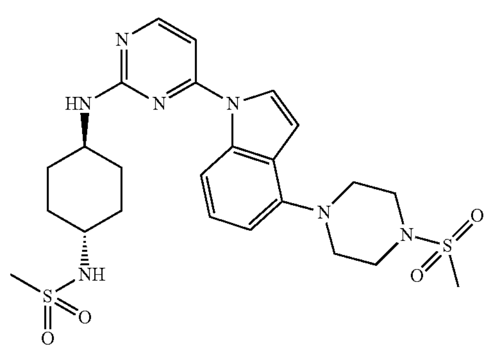 [SMILES: CS(=O)(=O)N[C@H]1CC[C@H](Nc2nccc(-n3ccc4c(N5CCN(S(C)(=O)=O)CC5)cccc43)n2)CC1] | N-(4-{4-[4-(4-Methanesulfonyl-piperazin-1-yl)-indol-1-yl]-pyrimidin-2-ylamino}-cyclohexyl)-methanesulfonamide |

TABLE X-continued

| | Structure | Nomenclature |
|---|---|---|
| I-4 | 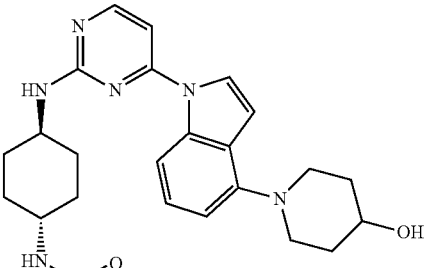 | N-(4-{4-[4-(4-Hydroxy-piperidin-1-yl)-indol-1-yl]-pyrimidin-2-ylamino}-cyclohexyl)-methanesulfonamide |
| | 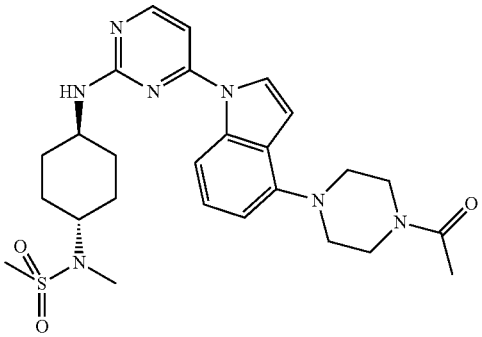 [SMILES: CC(=O)N1CCN(c2cccc3c2ccn3-c2ccnc(N[C@H]3CC[C@H](N(C)S(C)(=O)=O)CC3)n2)CC1] | N-(4-{4-[4-(4-Acetyl-piperazin-1-yl)-indol-1-yl]-pyrimidin-2-ylamino}-cyclohexyl)-N-methyl-methanesulfonamide |
| I-6 | 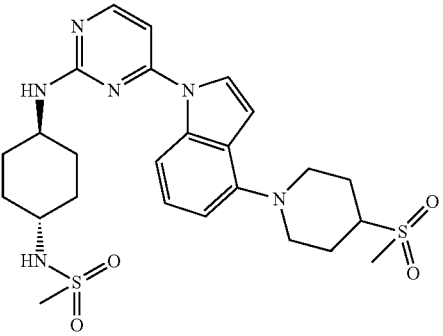 [SMILES: CS(=O)(=O)N[C@H]1CC[C@H](Nc2nccc(-n3ccc4c(N5CCC(S(C)(=O)=O)CC5)cccc43)n2)CC1] | N-(4-{4-[4-(4-Methanesulfonyl-piperidin-1-yl)-indol-1-yl]-pyrimidin-2-ylamino}-cyclohexyl)-methanesulfonamide |
| I-7 | 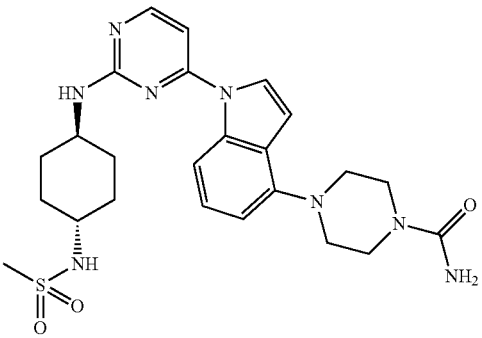 [SMILES: CS(=O)(=O)N[C@H]1CC[C@H](Nc2nccc(-n3ccc4c(N5CCN(C(N)=O)CC5)cccc43)n2)CC1] | 4-{1-[2-(4-Methanesulfonylamino-cyclohexylamino)-pyrimidin-4-yl]-1H-indol-4-yl}-piperazine-1-carboxylic acid amide |

TABLE X-continued

| | Structure | Nomenclature |
|---|---|---|
| I-8 | 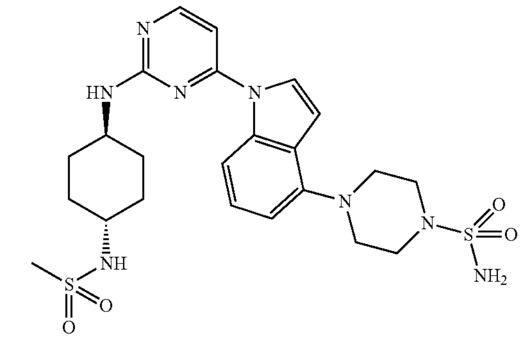 [SMILES: CS(=O)(=O)N[C@H]1CC[C@H](Nc2nccc(-n3ccc4c(N5CCN(S(N)(=O)=O)CC5)cccc43)n2)CC1] | 4-{1-[2-(4-Methanesulfonylamino-cyclohexylamino)-pyrimidin-4-yl]-1H-indol-4-yl}-piperazine-1-sulfonic acid amide |
| I-9 | 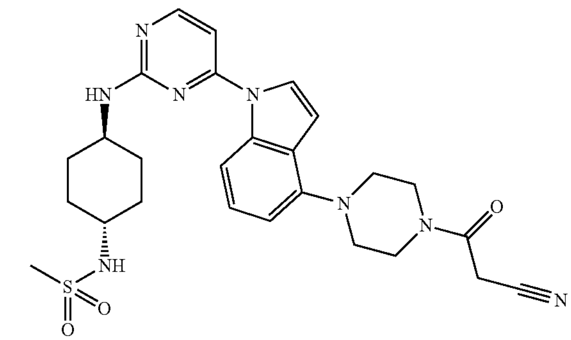 [SMILES: CS(=O)(=O)N[C@H]1CC[C@H](Nc2nccc(-n3ccc4c(N5CCN(C(=O)CC#N)CC5)cccc43)n2)CC1] | N-[4-(4-{4-[4-(2-Cyano-acetyl)-piperazin-1-yl]-indol-1-yl}-pyrimidin-2-ylamino)-cyclohexyl]-methanesulfonamide |
| I-10 | 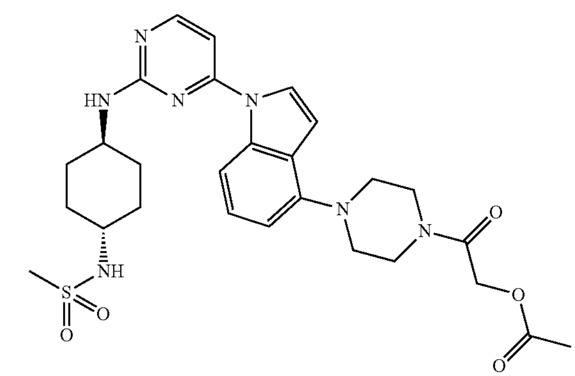 [SMILES: CC(=O)OCC(=O)N1CCN(c2cccc3c2ccn3-c2ccnc(N[C@H]3CC[C@H](NS(C)(=O)=O)CC3)n2)CC1] | Acetic acid 2-(4-{1-[2-(4-methanesulfonylamino-cyclohexylamino)-pyrimidin-4-yl]-1H-indol-4-yl}-piperazin-1-yl)-2-oxo-ethyl ester |
| I-11 | 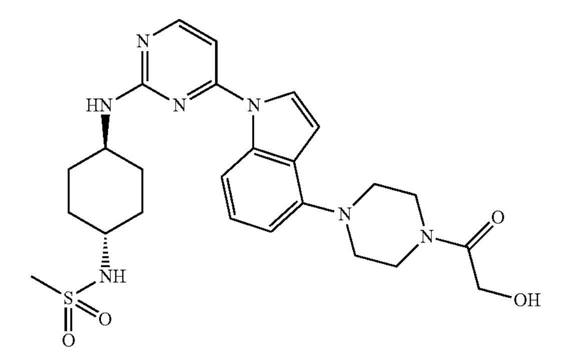 [SMILES: CS(=O)(=O)N[C@H]1CC[C@H](Nc2nccc(-n3ccc4c(N5CCN(C(=O)CO)CC5)cccc43)n2)CC1] | N-[4-(4-{4-[4-(2-Hydroxy-acetyl)-piperazin-1-yl]-indol-1-yl}-pyrimidin-2-ylamino)-cyclohexyl]-methanesulfonamide |

TABLE X-continued

| | Structure | Nomenclature |
|---|---|---|
| I-12 | 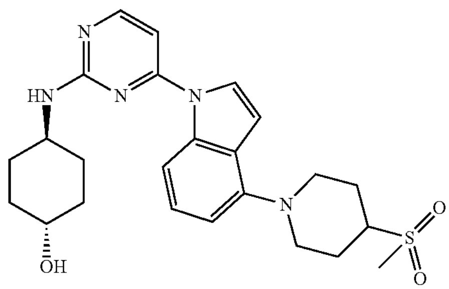 [SMILES: CS(=O)(=O)C1CCN(c2cccc3c2ccn3-c2ccnc(N[C@H]3CC[C@H](O)CC3)n2)CC1] | 4-{4-[4-(4-Methanesulfonyl-piperidin-1-yl)-indol-1-yl]-pyrimidin-2-ylamino}-cyclohexanol |
| I-13 | 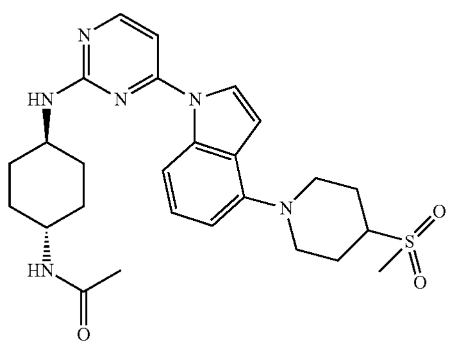 [SMILES: CC(=O)N[C@H]1CC[C@H](Nc2nccc(-n3ccc4c(N5CCC(S(C)(=O)=O)CC5)cccc43)n2)CC1] | N-(4-{4-[4-(4-Methanesulfonyl-piperidin-1-yl)-indol-1-yl]-pyrimidin-2-ylamino}-cyclohexyl)-acetamide |
| I-14 | 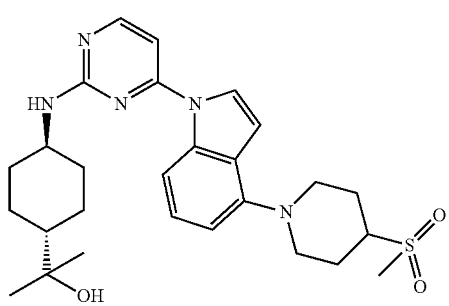 [SMILES: CC(C)(O)[C@H]1CC[C@H](Nc2nccc(-n3ccc4c(N5CCC(S(C)(=O)=O)CC5)cccc43)n2)CC1] | 2-(4-{4-[4-(4-Methanesulfonyl-piperidin-1-yl)-indol-1-yl]-pyrimidin-2-ylamino}-cyclohexyl)-propan-2-ol |
| I-15 | 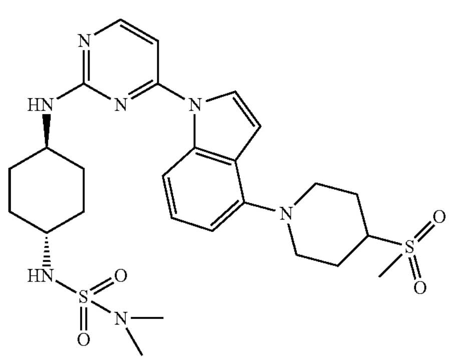 [SMILES: CN(C)S(=O)(=O)N[C@H]1CC[C@H](Nc2nccc(-n3ccc4c(N5CCC(S(C)(=O)=O)CC5)cccc43)n2)CC1] | [4-{4-[4-(4-Methanesulfonyl-piperidin-1-yl)-indol-1-yl]-pyrimidin-2-ylamino}-cyclohexyl] aminodimethylsulfonamide |
| I-16 | 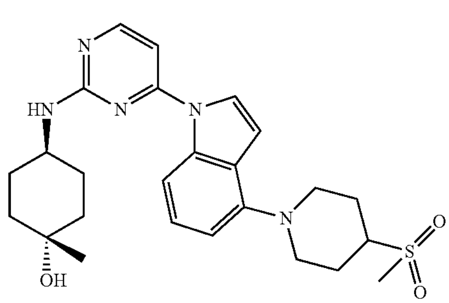 [SMILES: CS(=O)(=O)C1CCN(c2cccc3c2ccn3-c2ccnc(N[C@H]3CC[C@](C)(O)CC3)n2)CC1] | 4-{4-[4-(4-Methanesulfonyl-piperidin-1-yl)-indol-1-yl]-pyrimidin-2-ylamino}-1-methyl-cyclohexanol |

TABLE X-continued

| | Structure | Nomenclature |
|---|---|---|
| I-17 | 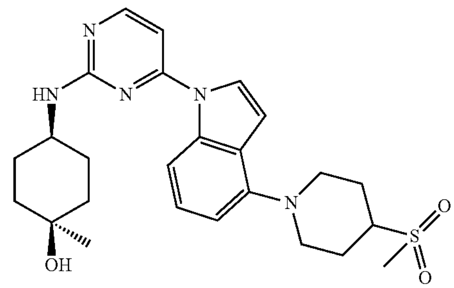 [SMILES: CS(=O)(=O)C1CCN(c2cccc3c2ccn3-c2ccnc(N[C@H]3CC[C@@](C)(O)CC3)n2)CC1] | 4-{4-[4-(4-Methanesulfonyl-piperidin-1-yl)-indol-1-yl]-pyrimidin-2-ylamino}-1-methyl-cyclohexanol |
| I-18 | 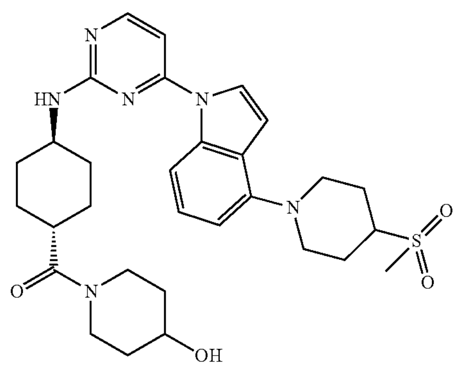 [SMILES: CS(=O)(=O)C1CCN(c2cccc3c2ccn3-c2ccnc(N[C@H]3CC[C@H](C(=O)N4CCC(O)CC4)CC3)n2)CC1] | (4-Hydroxy-piperidin-1-yl)-(4-{4-[4-(4-methanesulfonyl-piperidin-1-yl)-indol-1-yl]-pyrimidin-2-ylamino}-cyclohexyl)-methanone |
| I-19 | 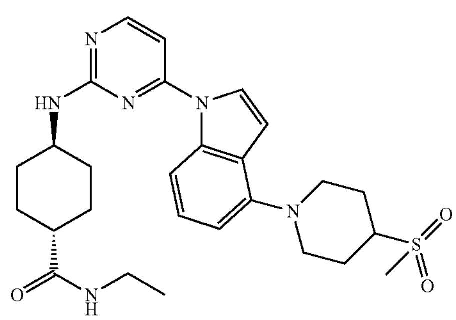 [SMILES: CCNC(=O)[C@H]1CC[C@H](Nc2nccc(-n3ccc4c(N5CCC(S(C)(=O)=O)CC5)cccc43)n2)CC1] | 4-{4-[4-(4-Methanesulfonyl-piperidin-1-yl)-indol-1-yl]-pyrimidin-2-ylamino}-cyclohexanecarboxylic acid ethylamide |
| I-20 | 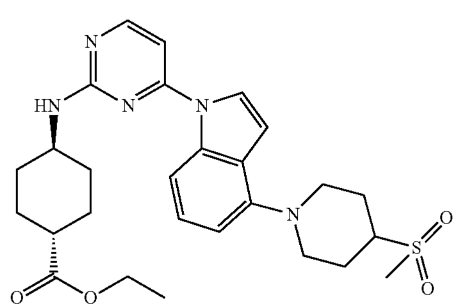 [SMILES: CCOC(=O)[C@H]1CC[C@H](Nc2nccc(-n3ccc4c(N5CCC(S(C)(=O)=O)CC5)cccc43)n2)CC1] | 4-{4-[4-(4-Methanesulfonyl-piperidin-1-yl)-indol-1-yl]-pyrimidin-2-amino}-cyclohexanecarboxylic acid ethyl ester |

TABLE X-continued

| | Structure | Nomenclature |
|---|---|---|
| I-21 | Chiral | 1-[(R)-4-(1-{2-[4-(4-Hydroxy-piperidine-1-carbonyl)-cyclohexylamino]-pyrimidin-4-yl}-1H-indol-4-yl)-3-methyl-piperazin-1-yl]-ethanone |
| I-22 | 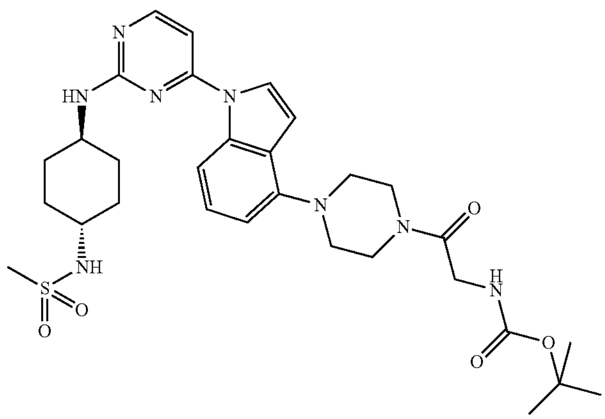 [SMILES: CC(C)(C)OC(=O)NCC(=O)N1CCN(c2cccc3c2ccn3-c2ccnc(N[C@H]3CC[C@H](NS(C)(=O)=O)CC3)n2)CC1] | [2-(4-{1-[2-(4-Methanesulfonylamino-cyclohexylamino)-pyrimidin-4-yl]-1H-indol-4-yl}-piperazin-1-yl)-2-oxo-ethyl]-carbamic acid tert-butyl ester |
| I-23 | 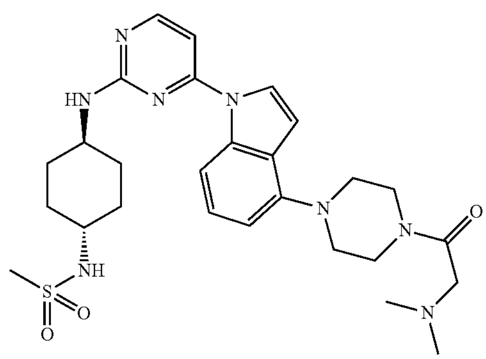 [SMILES: CN(C)CC(=O)N1CCN(c2cccc3c2ccn3-c2ccnc(N[C@H]3CC[C@H](NS(C)(=O)=O)CC3)n2)CC1] | N-[4-(4-{4-[4-(2-Dimethylamino-acetyl)-piperazin-1-yl]-indol-1-yl}-pyrimidin-2-ylamino)-cyclohexyl]-methanesulfonamide |
| I-24 | 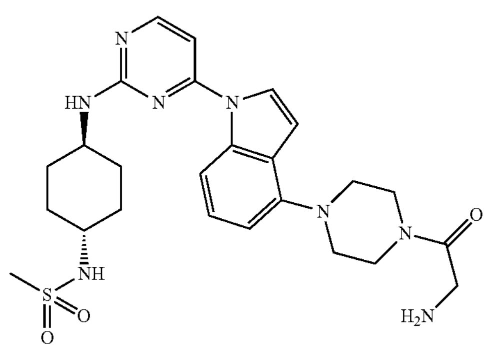 [SMILES: CS(=O)(=O)N[C@H]1CC[C@H](Nc2nccc(-n3ccc4c(N5CCN(C(=O)CN)CC5)cccc43)n2)CC1] | N-[4-(4-{4-[4-(2-Amino-acetyl)-piperazin-1-yl]-indol-1-yl}-pyrimidin-2-ylamino)-cyclohexyl]-methanesulfonamide |

TABLE X-continued

| | Structure | | Nomenclature |
|---|---|---|---|
| I-25 | 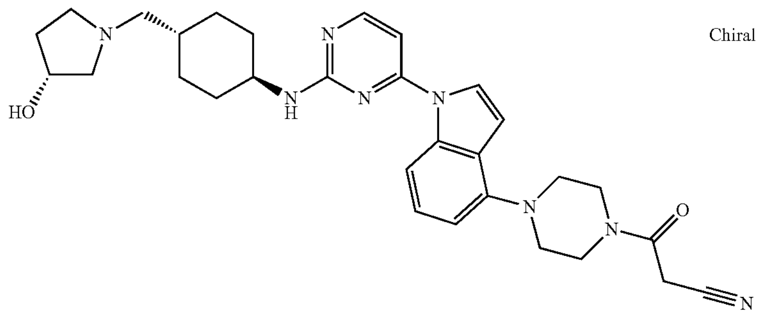 [SMILES: N#CCC(=O)N1CCN(c2cccc3c2ccn3-c2ccnc(N[C@H]3CC[C@H](CN4CC[C@@H](O)C4)CC3)n2)CC1 ; "Chiral"] | Chiral | 3-[4-(1-{2-[4-((R)-3-Hydroxy-pyrrolidin-1-ylmethyl)-cyclohexylamino]-pyrimidin-4-yl}-1H-indol-4-yl)-piperazin-1-yl]-3-oxo-propionitrile |
| I-26 | 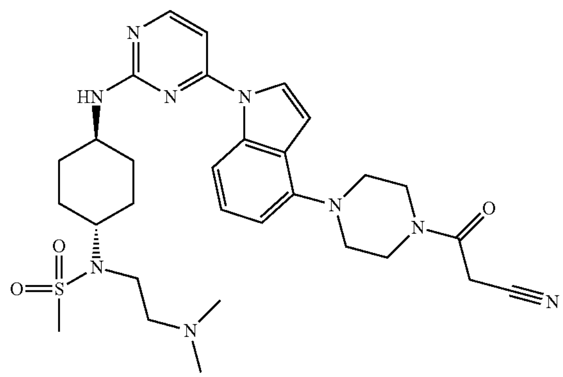 [SMILES: CN(C)CCN([C@H]1CC[C@H](Nc2nccc(-n3ccc4c(N5CCN(C(=O)CC#N)CC5)cccc43)n2)CC1)S(C)(=O)=O] | | N-[4-(4-{4-[4-(2-Cyano-acetyl)-piperazin-1-yl]-indol-1-yl}-pyrimidin-2-ylamino)-cyclohexyl]-N-(2-dimethylamino-ethyl)-methanesulfonamide |
| I-27 | 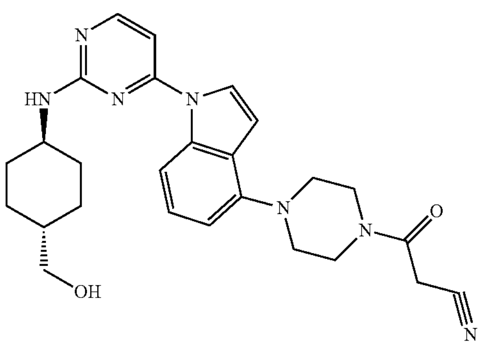 [SMILES: N#CCC(=O)N1CCN(c2cccc3c2ccn3-c2ccnc(N[C@H]3CC[C@H](CO)CC3)n2)CC1] | | 3-(4-{1-[2-(4-Hydroxymethyl-cyclohexylamino)-pyrimidin-4-yl]-1H-indol-4-yl}-piperazin-1-yl)-3-oxo-propionitrile |
| I-28 | 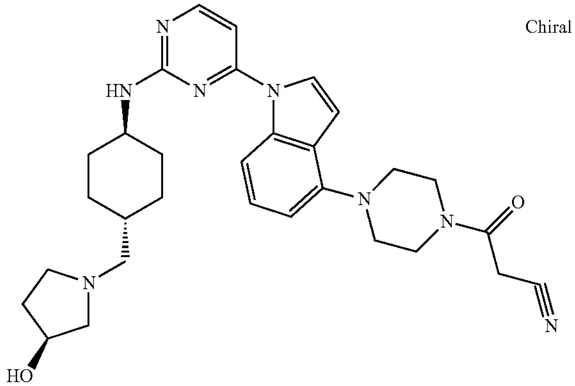 [SMILES: N#CCC(=O)N1CCN(c2cccc3c2ccn3-c2ccnc(N[C@H]3CC[C@H](CN4CC[C@H](O)C4)CC3)n2)CC1 ; "Chiral"] | Chiral | 3-[4-(1-{2-[4-((S)-3-Hydroxy-pyrrolidin-1-ylmethyl)-cyclohexylamino]-pyrimidin-4-yl}-1H-indol-4-yl)-piperazin-1-yl]-3-oxo-propionitrile |

TABLE X-continued

| | Structure | Nomenclature |
|---|---|---|
| I-29 | 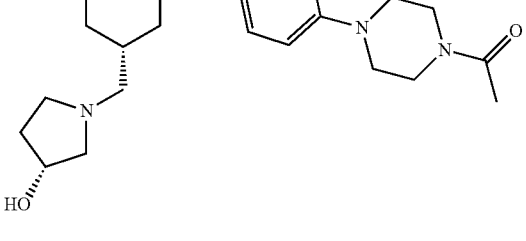 Chiral | 1-[4-(1-{2-[4-((R)-3-Hydroxy-pyrrolidin-1-ylmethyl)-cyclohexylamino]-pyrimidin-4-yl}-1H-indol-4-yl)-piperazin-1-yl]-ethanone |
| I-30 | 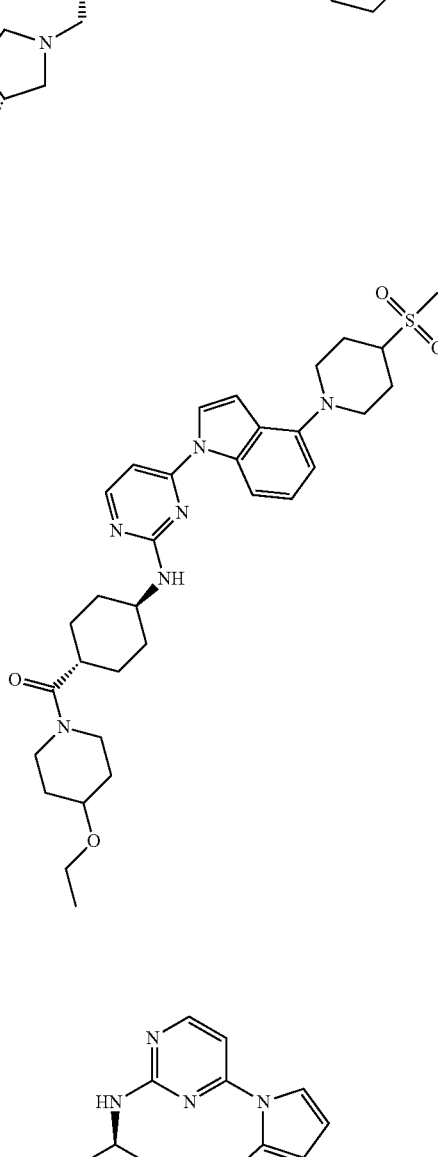 | (4-Ethoxy-piperidin-1-yl)-(4-{4-[4-(4-methanesulfonyl-piperidin-1-yl)-indol-1-yl]-pyrimidin-2-ylamino}-cyclohexyl)-methanone |
| I-31 | 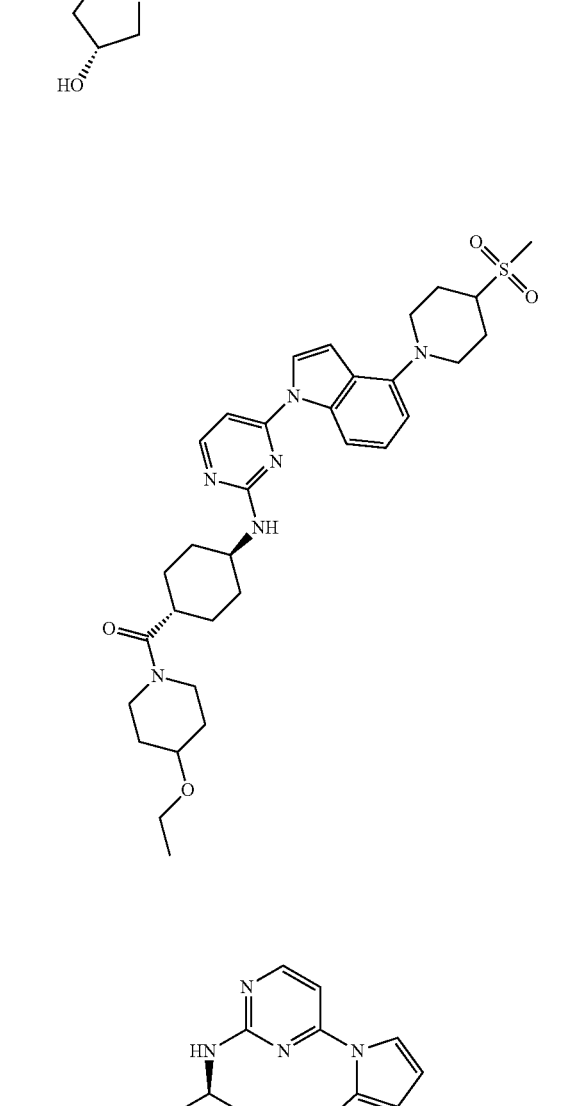 Chiral | ((R)-3-Ethoxy-pyrrolidin-1-yl)-(4-{4-[4-(4-methanesulfonyl-piperidin-1-yl)-indol-1-yl]-pyrimidin-2-ylamino}-cyclohexyl)-methanone |

TABLE X-continued

| | Structure | Nomenclature |
|---|---|---|
| I-32 | *(Chiral)* | ((S)-3-Ethoxy-pyrrolidin-1-yl)-(4-{4-[4-(4-methanesulfonyl-piperidin-1-yl)-indol-1-yl]-pyrimidin-2-ylamino}-cyclohexyl)-methanone |
| I-33 | 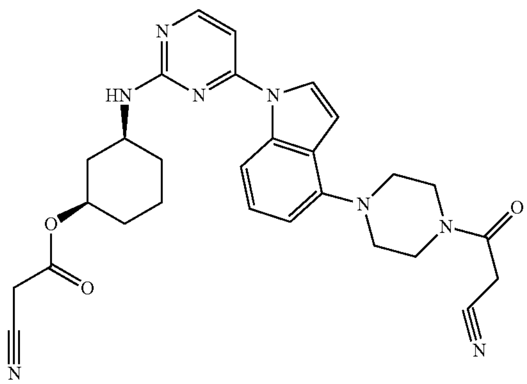 [SMILES: N#CCC(=O)O[C@@H]1CCC[C@H](Nc2nccc(-n3ccc4c(N5CCN(C(=O)CC#N)CC5)cccc43)n2)C1] | Cyano-acetic acid (1R,3S)-3-(4-{4-[4-(2-cyano-acetyl)-piperazin-1-yl]-indol-1-yl}-pyrimidin-2-ylamino)-cyclohexyl ester |
| I-34 | 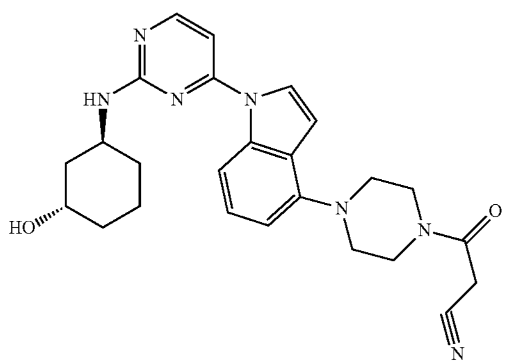 [SMILES: N#CCC(=O)N1CCN(c2cccc3c2ccn3-c2ccnc(N[C@H]3CCC[C@H](O)C3)n2)CC1] | 3-(4-{1-[2-((1S,3S)-3-Hydroxy-cyclohexylamino)-pyrimidin-4-yl]-1H-indol-4-yl}-piperazin-1-yl)-3-oxo-propionitrile |
| I-35 | 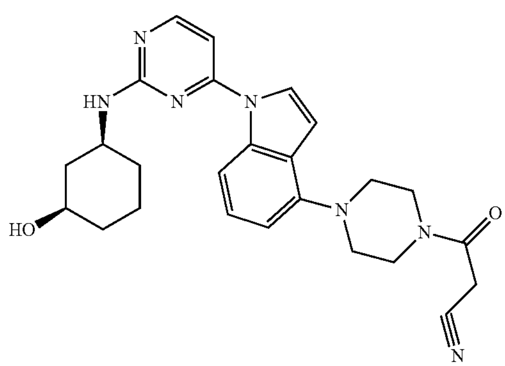 [SMILES: N#CCC(=O)N1CCN(c2cccc3c2ccn3-c2ccnc(N[C@H]3CCC[C@@H](O)C3)n2)CC1] | 3-(4-{1-[2-((1S,3R)-3-Hydroxy-cyclohexylamino)-pyrimidin-4-yl]-1H-indol-4-yl}-piperazin-1-yl)-3-oxo-propionitrile |

TABLE X-continued
| | Structure | Nomenclature |
|---|---|---|
| I-36 | 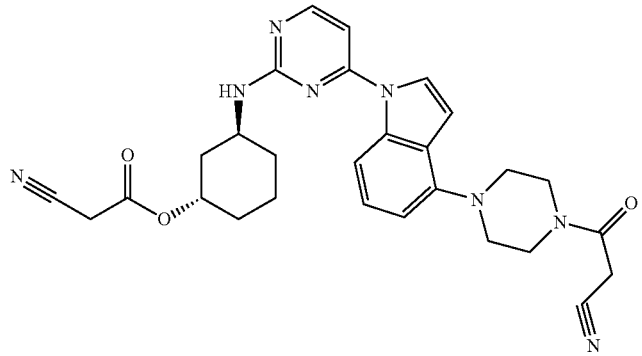 [SMILES: N#CCC(=O)O[C@H]1CCC[C@H](Nc2nccc(-n3ccc4c(N5CCN(C(=O)CC#N)CC5)cccc43)n2)C1] | Cyano-acetic acid (1S,3S)-3-(4-{4-[4-(2-cyano-acetyl)-piperazin-1-yl]-indol-1-yl}-pyrimidin-2-ylamino)-cyclohexyl ester |
| I-37 | 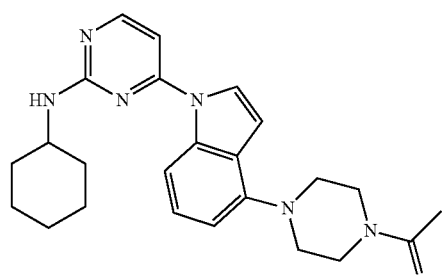 | 1-{4-[1-(2-Cyclohexylamino-pyrimidin-4-yl)-1H-indol-4-yl]-piperazin-1-yl}-ethanone |
| I-38 | 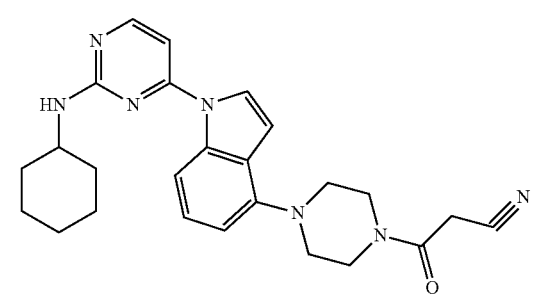 [SMILES: N#CCC(=O)N1CCN(c2cccc3c2ccn3-c2ccnc(NC3CCCCC3)n2)CC1] | 3-{4-[1-(2-Cyclohexylamino-pyrimidin-4-yl)-1H-indol-4-yl]-piperazin-1-yl}-3-oxo-propionitrile |
| I-39 | 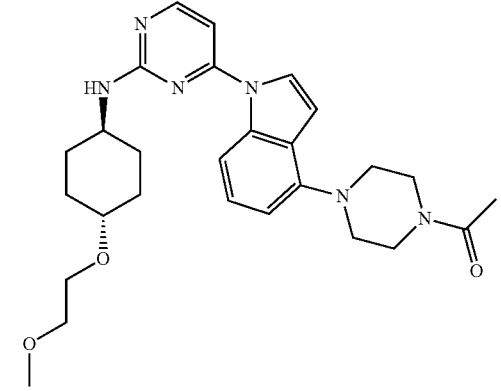 [SMILES: COCCO[C@H]1CC[C@H](Nc2nccc(-n3ccc4c(N5CCN(C(C)=O)CC5)cccc43)n2)CC1] | 1-[4-(1-{2-[4-(2-Methoxy-ethoxy)-cyclohexylamino]-pyrimidin-4-yl}-1H-indol-4-yl)-piperazin-1-yl]-ethanone |

TABLE X-continued

| | Structure | Nomenclature |
|---|---|---|
| I-40 | 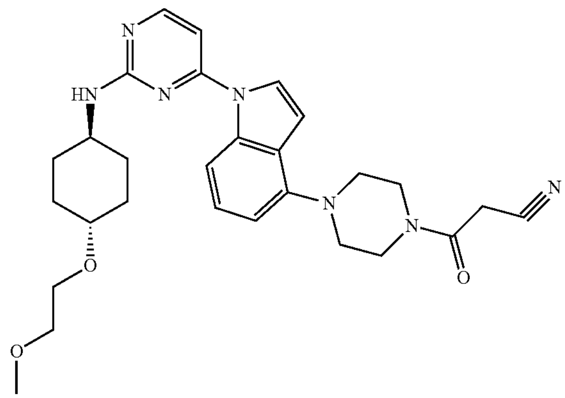 [SMILES: COCCO[C@H]1CC[C@H](Nc2nccc(-n3ccc4c(N5CCN(C(=O)CC#N)CC5)cccc43)n2)CC1] | 3-[4-(1-{2-[4-(2-Methoxy-ethoxy)-cyclohexylamino]-pyrimidin-4-yl}-1H-indol-4-yl)-piperazin-1-yl]-3-oxo-propionitrile |
| I-41 | 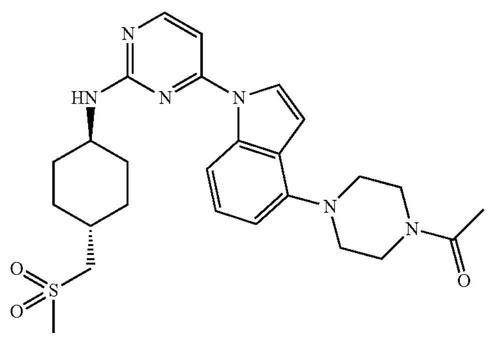 [SMILES: CC(=O)N1CCN(c2cccc3c2ccn3-c2ccnc(N[C@H]3CC[C@H](CS(C)(=O)=O)CC3)n2)CC1] | 1-(4-{1-[2-(4-Methanesulfonylmethyl-cyclohexylamino)-pyrimidin-4-yl]-1H-indol-4-yl}-piperazin-1-yl)-ethanone |
| I-42 | 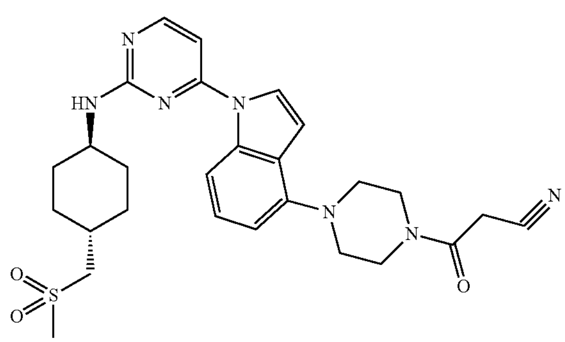 [SMILES: CS(=O)(=O)C[C@H]1CC[C@H](Nc2nccc(-n3ccc4c(N5CCN(C(=O)CC#N)CC5)cccc43)n2)CC1] | 3-(4-{1-[2-(4-Methanesulfonylmethyl-cyclohexylamino)-pyrimidin-4-yl]-1H-indol-4-yl}-piperazin-1-yl)-3-oxo-propionitrile |
| I-43 | 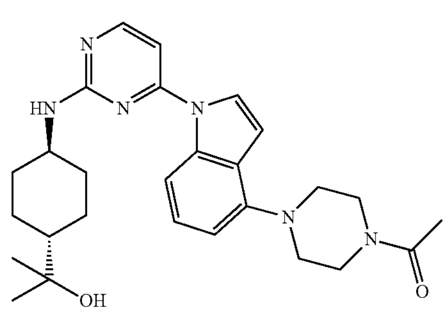 [SMILES: CC(=O)N1CCN(c2cccc3c2ccn3-c2ccnc(N[C@H]3CC[C@H](C(C)(C)O)CC3)n2)CC1] | 1-[4-(1-{2-[4-(1-Hydroxy-1-methyl-ethyl)-cyclohexylamino]-pyrimidin-4-yl}-1H-indol-4-yl)-piperazin-1-yl]-ethanone |

TABLE X-continued
| | Structure | Nomenclature |
|---|---|---|
| I-44 | 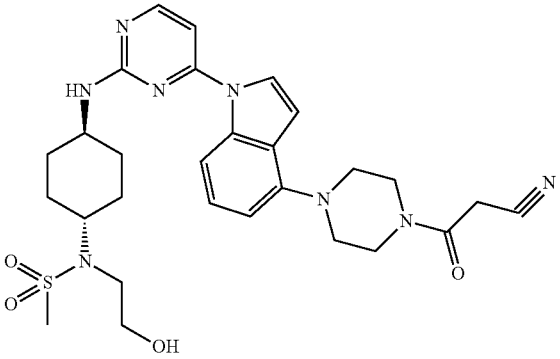 [SMILES: CS(=O)(=O)N(CCO)[C@H]1CC[C@H](Nc2nccc(-n3ccc4c(N5CCN(C(=O)CC#N)CC5)cccc43)n2)CC1] | N-[4-(4-{4-[4-(2-Cyano-acetyl)-piperazin-1-yl]-indol-1-yl}-pyrimidin-2-ylamino)-cyclohexyl]-N-(2-hydroxy-ethyl)-methanesulfonamide |
| I-45 | 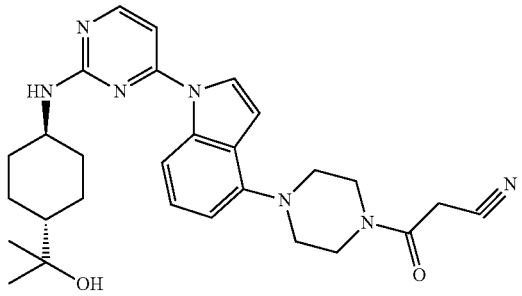 [SMILES: CC(C)(O)[C@H]1CC[C@H](Nc2nccc(-n3ccc4c(N5CCN(C(=O)CC#N)CC5)cccc43)n2)CC1] | 3-[4-(1-{2-[4-(1-Hydroxy-1-methyl-ethyl)-cyclohexylamino]-pyrimidin-4-yl}-1H-indol-4-yl)-piperazin-1-yl]-3-oxo-propionitrile |
| I-46 | 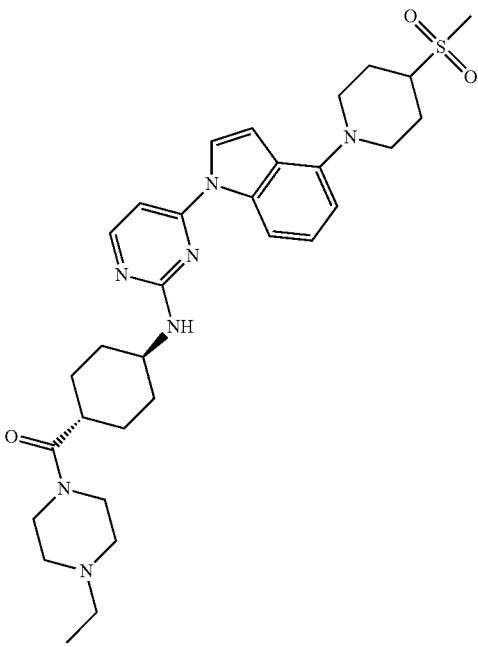 [SMILES: CCN1CCN(C(=O)[C@H]2CC[C@H](Nc3nccc(-n4ccc5c(N6CCC(S(C)(=O)=O)CC6)cccc54)n3)CC2)CC1] | (4-Ethyl-piperazin-1-yl)-(4-{4-[4-(4-methanesulfonyl-piperidin-1-yl)-indol-1-yl]-pyrimidin-2-ylamino}-cyclohexyl)-methanone |

TABLE X-continued
| | Structure | Nomenclature |
|---|---|---|
| I-47 | 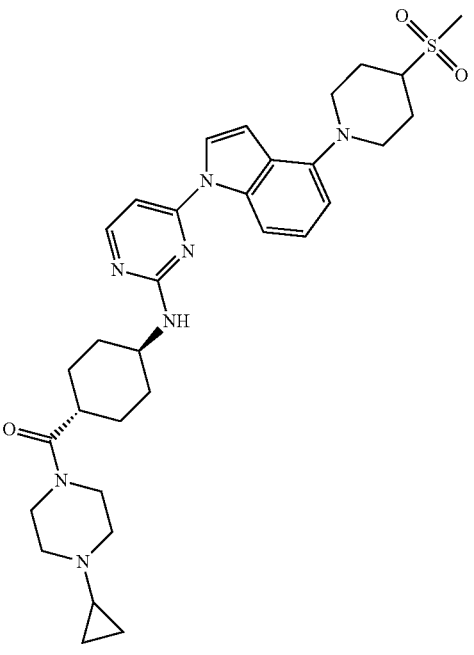 [SMILES: CS(=O)(=O)C1CCN(c2cccc3c2ccn3-c2ccnc(N[C@H]3CC[C@H](C(=O)N4CCN(C5CC5)CC4)CC3)n2)CC1] | (4-Cyclopropyl-piperazin-1-yl)-(4-{4-[4-(4-methanesulfonyl-piperidin-1-yl)-indol-1-yl]-pyrimidin-2-ylamino}-cyclohexyl)-methanone |
| I-48 | 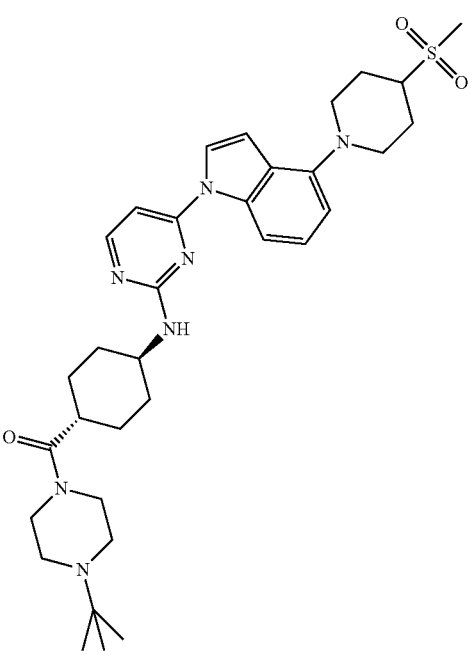 [SMILES: CC(C)(C)N1CCN(C(=O)[C@H]2CC[C@H](Nc3nccc(-n4ccc5c(N6CCC(S(C)(=O)=O)CC6)cccc54)n3)CC2)CC1] | (4-tert-Butyl-piperazin-1-yl)-(4-{4-[4-(4-methanesulfonyl-piperidin-1-yl)-indol-1-yl]-pyrimidin-2-ylamino}-cyclohexyl)-methanone |

TABLE X-continued
| Structure | Nomenclature |
|---|---|
| I-49 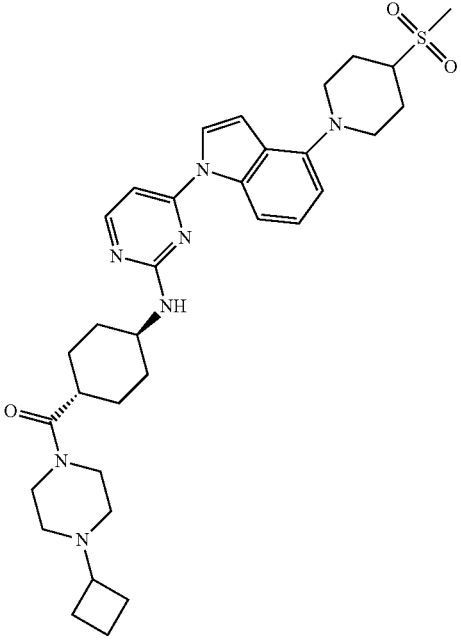 [SMILES: CS(=O)(=O)C1CCN(c2cccc3c2ccn3-c2ccnc(N[C@H]3CC[C@H](C(=O)N4CCN(C5CCC5)CC4)CC3)n2)CC1] | (4-Cyclobutyl-piperazin-1-yl)-(4-{4-[4-(4-methanesulfonyl-piperidin-1-yl)-indol-1-yl]-pyrimidin-2-ylamino}-cyclohexyl)-methanone |
| I-50 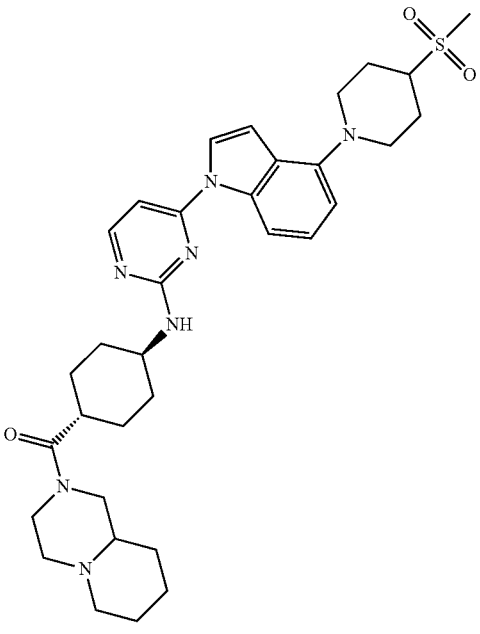 [SMILES: CS(=O)(=O)C1CCN(c2cccc3c2ccn3-c2ccnc(N[C@H]3CC[C@H](C(=O)N4CCN5CCCCC5C4)CC3)n2)CC1] | (4-{4-[4-(4-Methanesulfonyl-piperidin-1-yl)-indol-1-yl]-pyrimidin-2-ylamino}-cyclohexyl)-(octahydro-pyrido[1,2-a]pyrazin-2-yl)-methanone |

TABLE X-continued
| | Structure | Nomenclature |
|---|---|---|
| I-51 | 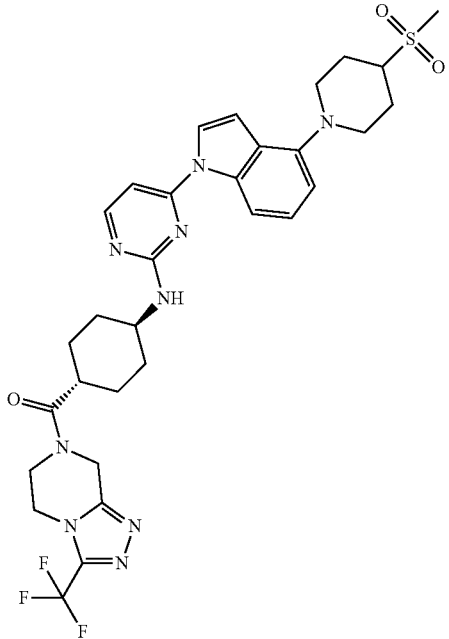 [SMILES: CS(=O)(=O)C1CCN(c2cccc3c2ccn3-c2ccnc(N[C@H]3CC[C@H](C(=O)N4CCn5c(nnc5C(F)(F)F)C4)CC3)n2)CC1] | (4-{4-[4-(4-Methanesulfonyl-piperidin-1-yl)-indol-1-yl]-pyrimidin-2-ylamino}-cyclohexyl)-(3-trifluoromethyl-5,6-dihydro-8H-[1,2,4]triazolo[4,3-a]pyrazin-7-yl)-methanone |
| I-52 | 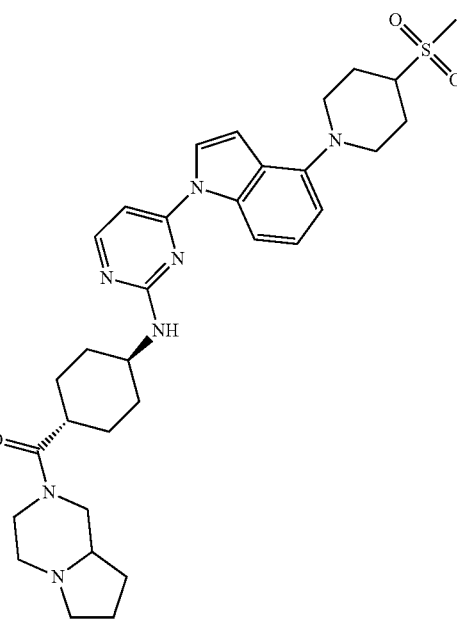 | (Hexahydro-pyrrolo[1,2-a]pyrazin-2-yl)-(4-{4-[4-(4-methanesulfonyl-piperidin-1-yl)-indol-1-yl]-pyrimidin-2-ylamino}-cyclohexyl)-methanone |

TABLE X-continued

| | Structure | Nomenclature |
|---|---|---|
| I-53 | 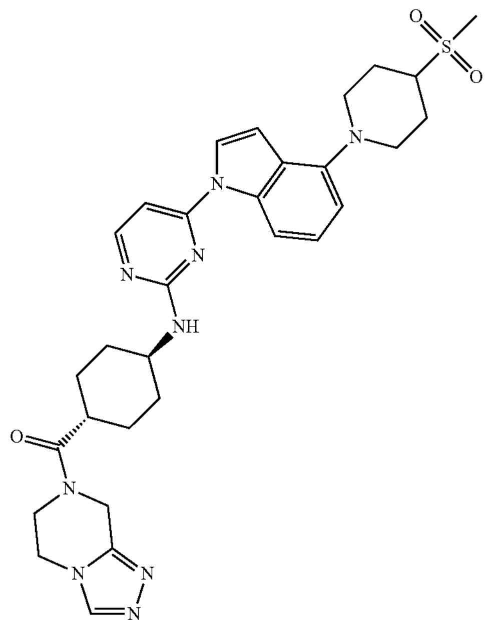 [SMILES: CS(=O)(=O)C1CCN(c2cccc3c2ccn3-c2ccnc(N[C@H]3CC[C@H](C(=O)N4CCn5cnnc5C4)CC3)n2)CC1] | (5,6-Dihydro-8H-[1,2,4]triazolo[4,3-a]pyrazin-7-yl)-(4-{4-[4-(4-methanesulfonyl-piperidin-1-yl)-indol-1-yl]-pyrimidin-2-ylamino}-cyclohexyl)-methanone |
| I-54 | 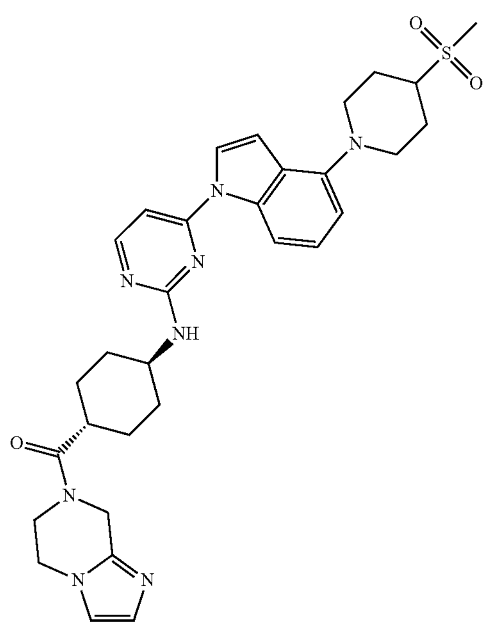 [SMILES: CS(=O)(=O)C1CCN(c2cccc3c2ccn3-c2ccnc(N[C@H]3CC[C@H](C(=O)N4CCn5ccnc5C4)CC3)n2)CC1] | (5,6-Dihydro-8H-imidazo[1,2-a]pyrazin-7-yl)-(4-{4-[4-(4-methanesulfonyl-piperidin-1-yl)-indol-1-yl]-pyrimidin-2-ylamino}-cyclohexyl)-methanone |
| I-55 | 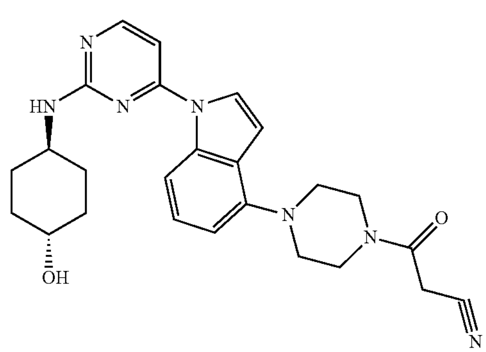 [SMILES: N#CCC(=O)N1CCN(c2cccc3c2ccn3-c2ccnc(N[C@H]3CC[C@H](O)CC3)n2)CC1] | 3-(4-{1-[2-(4-Hydroxy-cyclohexylamino)-pyrimidin-4-yl]-1H-indol-4-yl}-piperazin-1-yl)-3-oxo-propionitrile |

TABLE X-continued

| | Structure | Nomenclature |
|---|---|---|
| I-56 | 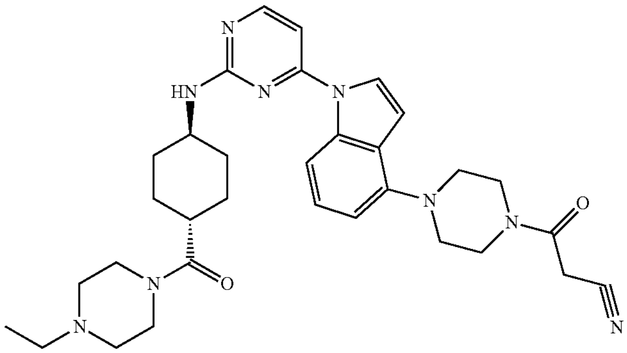 [SMILES: CCN1CCN(C(=O)[C@H]2CC[C@H](Nc3nccc(-n4ccc5c(N6CCN(C(=O)CC#N)CC6)cccc54)n3)CC2)CC1] | 3-[4-(1-{2-[4-(4-Ethyl-piperazine-1-carbonyl)-cyclohexylamino]-pyrimidin-4-yl}-1H-indol-4-yl)-piperazin-1-yl]-3-oxo-propionitrile |
| I-57 | 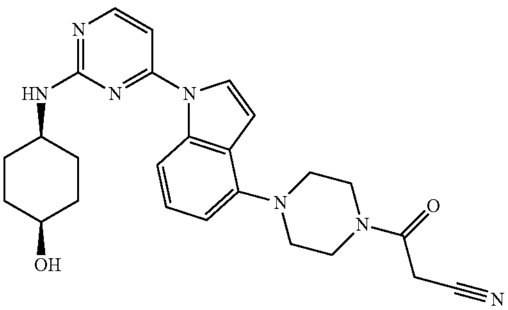 [SMILES: N#CCC(=O)N1CCN(c2cccc3c2ccn3-c2ccnc(N[C@H]3CC[C@@H](O)CC3)n2)CC1] | 3-(4-{1-[2-(4-Hydroxy-cyclohexylamino)-pyrimidin-4-yl]-1H-indol-4-yl}-piperazin-1-yl)-3-oxo-propionitrile |
| I-58 | Chiral | 3-(4-{1-[2-((1S,3R)-3-Hydroxy-cyclopentylamino)-pyrimidin-4-yl]-1H-indol-4-yl}-piperazin-1-yl)-3-oxo-propionitrile |
| I-59 | Chiral | 3-(4-{1-[2-((1R,3S)-3-Hydroxy-cyclopentylamino)-pyrimidin-4-yl]-1H-indol-4-yl}-piperazin-1-yl)-3-oxo-propionitrile |
| I-60 | Chiral | 3-(4-{1-[2-((1S,3S)-3-Hydroxy-cyclopentylamino)-pyrimidin-4-yl]-1H-indol-4-yl}-piperazin-1-yl)-3-oxo-propionitrile |

TABLE X-continued

| | Structure | Nomenclature |
|---|---|---|
| I-61 | 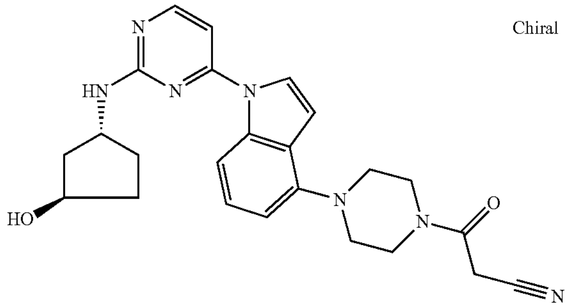 [SMILES: N#CCC(=O)N1CCN(c2cccc3c2ccn3-c2ccnc(N[C@@H]3CC[C@@H](O)C3)n2)CC1 ; "Chiral"] | 3-(4-{1-[2-((1R,3R)-3-Hydroxy-cyclopentylamino)-pyrimidin-4-yl]-1H-indol-4-yl}-piperazin-1-yl)-3-oxo-propionitrile |
| I-62 | 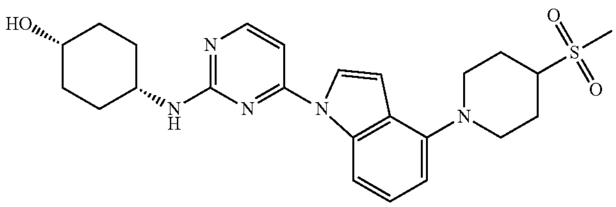 [SMILES: CS(=O)(=O)C1CCN(c2cccc3c2ccn3-c2ccnc(N[C@H]3CC[C@@H](O)CC3)n2)CC1] | 4-{4-[4-(4-Methanesulfonyl-piperidin-1-yl)-indol-1-yl]-pyrimidin-2-ylamino}-cyclohexanol |
| I-63 | 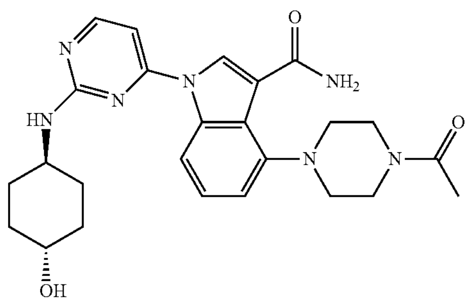 [SMILES: CC(=O)N1CCN(c2cccc3c2c(C(N)=O)cn3-c2ccnc(N[C@H]3CC[C@H](O)CC3)n2)CC1] | 4-(4-Acetyl-piperazin-1-yl)-1-[2-(4-hydroxy-cyclohexylamino)-pyrimidin-4-yl]-1H-indole-3-carboxylic acid amide |
| I-64 | 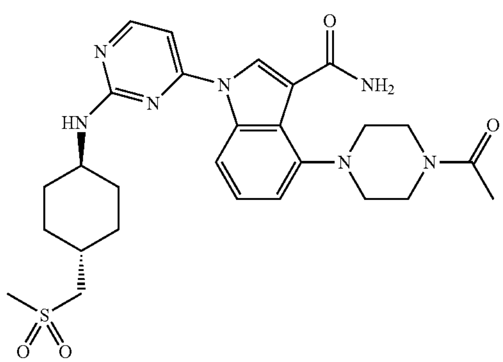 [SMILES: CC(=O)N1CCN(c2cccc3c2c(C(N)=O)cn3-c2ccnc(N[C@H]3CC[C@H](CS(C)(=O)=O)CC3)n2)CC1] | 4-(4-Acetyl-piperazin-1-yl)-1-[2-(4-methanesulfonylmethyl-cyclohexylamino)-pyrimidin-4-yl]-1H-indole-3-carboxylic acid amide |
| I-65 | 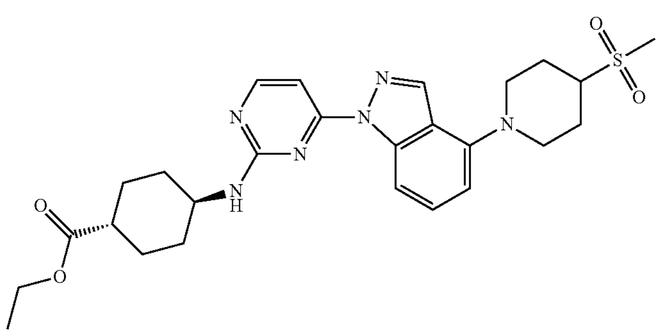 [SMILES: CCOC(=O)[C@H]1CC[C@H](Nc2nccc(-n3ncc4c(N5CCC(S(C)(=O)=O)CC5)cccc43)n2)CC1] | 4-{4-[4-(4-Methanesulfonyl-piperidin-1-yl)-indazol-1-yl]-pyrimidin-2-ylamino}-cyclohexanecarboxylic acid ethyl ester |

TABLE X-continued

| | Structure | Nomenclature |
|---|---|---|
| I-66 | 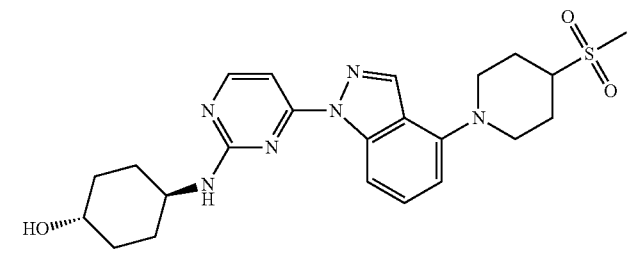 [SMILES: CS(=O)(=O)C1CCN(c2cccc3c2cnn3-c2ccnc(N[C@H]3CC[C@H](O)CC3)n2)CC1] | 4-{4-[4-(4-Methanesulfonyl-piperidin-1-yl)-indazol-1-yl]-pyrimidin-2-ylamino}-cyclohexanol |

Utility

The compounds of this invention are JNK inhibitors and as such are expected to be effective in the treatment of a wide range of JNK mediated disorders. Exemplary JNK mediated disorders include, but are not limited to, autoimmune disorders, inflammatory disorders, metabolic disorders, neurological disease, and cancer. Accordingly, compounds of the invention can be used to treat one or more of such disorders. In some embodiments, compounds of the invention can be used to treat a JNK mediated disorder such as rheumatoid arthritis, asthma, type II diabetes, Alzheimer's disease, Parkinson's disease or stroke.

Administration and Pharmaceutical Compositions

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use.

Formulations containing about one (1) mg of active ingredient or, more broadly, about 0.01 to about one hundred (100) mg, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxy-methylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the invention may also be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chloro-fluorocarbon (CFC), for example, dichlorodifluoromethane, trichlorofluoromethane, or dichloro-tetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacyclo-heptan-2-one). Sustained release delivery systems are inserted subcutaneously into the sub-dermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

Additional objects, advantages, and novel features of this invention will become apparent to those skilled in the art upon examination of the following examples thereof, which are not intended to be limiting.

| LIST OF ABBREVIATIONS | |
|---|---|
| $Ac_2O$ | Acetic anhydride |
| AcOH | Acetic acid |
| DBU | 1,8-Diazabicyclo[5.4.0]undec-7-ene |
| DCE | 1,2-Dichloroethane |
| DCM | Dichloromethane/Methylene chloride |
| DIPEA | Diisopropylethylamine |
| DMF | N,N-dimethylformamide |
| DMSO | Dimethyl sulfoxide |

LIST OF ABBREVIATIONS

| | |
|---|---|
| EDCI | 1-(3-Dimethylaminopropyl)-3-ethylcarbodiimide hydrochloride |
| Et$_2$O | Diethyl ether |
| EtOH | Ethanol/Ethyl alcohol |
| EtOAc | Ethyl acetate |
| HOBt | 1-Hydroxybenzotriazole |
| LDA | Lithium diisopropylamide |
| LiHMDS | Lithium bis(trimethylsilyl)amide |
| m-CPBA | 3-Chloroperoxybenzoic acid |
| MeOH | Methanol/Methyl alcohol |
| MW | Microwaves |
| NMP | 1-Methyl-2-pyrrolidinone |
| PMB | 4-Methoxy benzyl |
| RT | Room temperature |
| TBME | tert-Butyl methyl ether |
| TFA | Trifluoroacetic acid |
| Tf$_2$O | Trifluoromethanesulfonic anhydride |
| THF | Tetrahydrofuran |
| TLC | Thin layer chromatography |

EXAMPLES

The following preparations and examples are given to enable those skilled in the art to more clearly understand and to practice the present invention. They should not be considered as limiting the scope of the invention, but merely as being illustrative and representative thereof.

Example 1

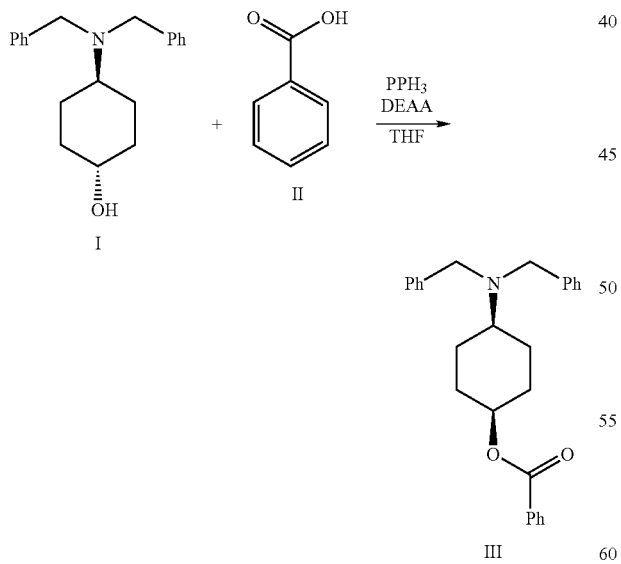

5.23 g of I in 100 mL THF was treated with 2.6 g of II, 4.65 g PPH$_3$, and 8.4 mL DEAA. The mixture was then diluted with EtOAc, washed with water, dried over Na$_2$SO$_4$, filtered, and concentrated in vacuo. The residue was triturated with hexane and the resultant solid filtered off and the filtrate was concentrated in vacuo and purified on a column using 100% hexane to 15:1 EtOAc:hexane to yield product III.

Example 2

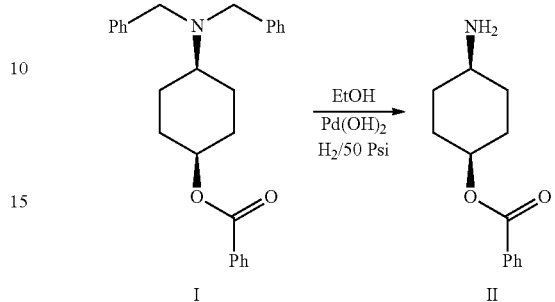

0.75 g of I in 100 mL EtOH was treated with 0.15 g Pd(OH)$_2$, purged with N$_2$, and then treated with H$_2$ at 50 psi for 2 days. The mixture was then filtered, dried in vacuo to yield 0.39 g of II.

Example 3

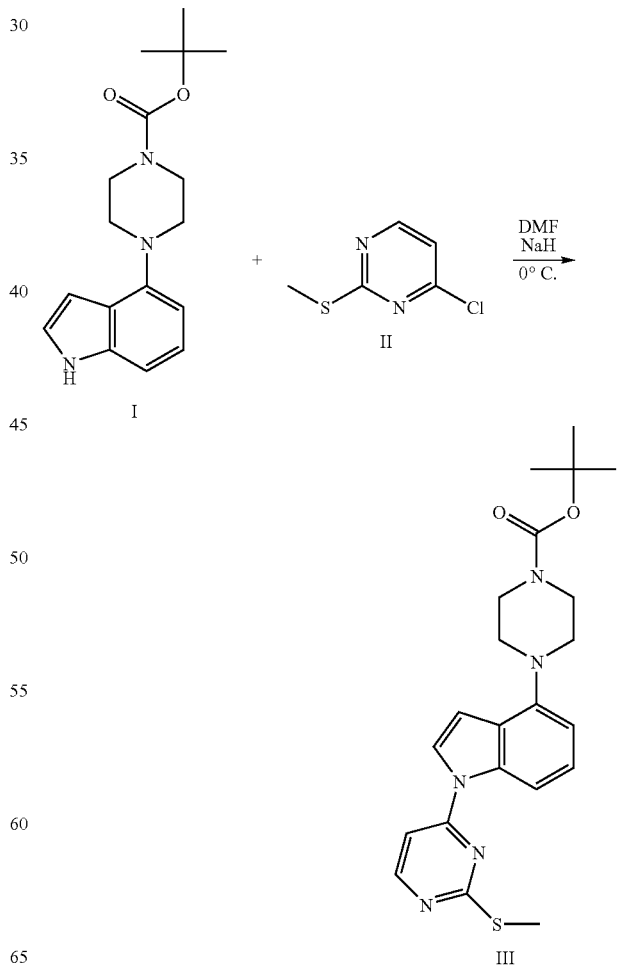

10.53 g of I in 100 mL DMF and cooled to 0° C. was gradually treated with 1.54 g NaH and stirred at 0° C. for 1 h followed by the dropwise addition of 4.4 mL of II and stirred for 4 h at 0° C. The mixture was diluted with water and the solid separated and was filtered, washed with water, and dried. The solid was then triturated with EtOAc/hexane and filtered and dried to yield 14 g of III.

Example 4

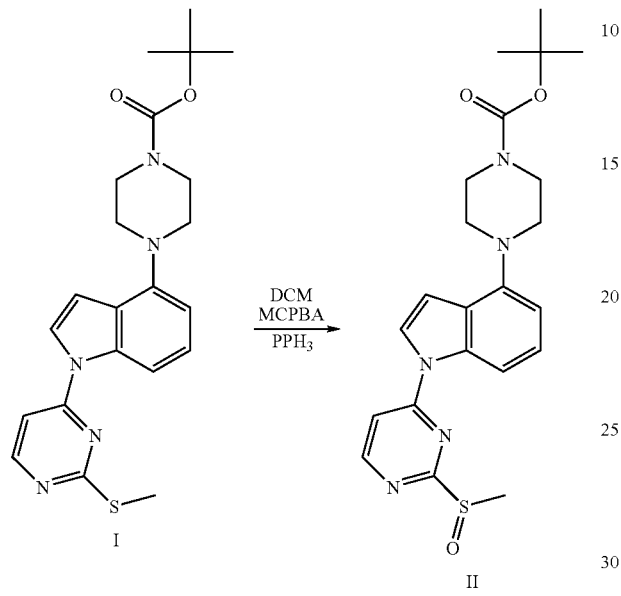

14 g of I in 500 mL DCM cooled to 0° C. was treated with 14.72 g of MCPBA and allowed to stir at 0° C. for 2 h. 25.8 g PPh$_3$ was then added and stirred at rt overnight. The mixture was then washed with saturated NaHCO$_3$ solution and the organic layer was separated and dried over Na$_2$SO$_4$, filtered and concentrated in vacuo. The residue was then triturated with hot EtOAc and the solid was filtered, dried at 50° C. in vacuo to yield 11 g of II.

Example 5

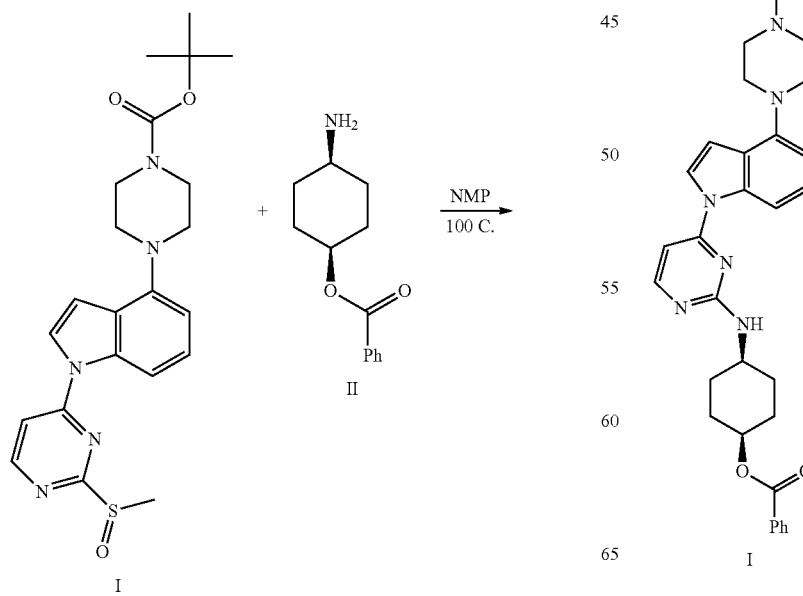

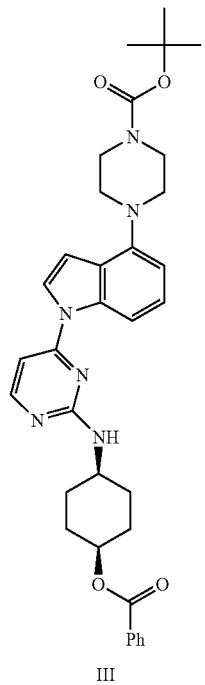

0.26 g of I in 2 mL NMP was treated with 0.39 g of II and allowed to stir at 100° C. for 5 h, cooled to r.t., diluted with water, the solid separated, filtered and dried. The solid was purified by silica column using 100% DCM to 5% MeOH/DCM. The fractions containing the product were concentrated in vacuo and triturated with EtOAc. The solid was filtered and dried to yield 0.225 g of III.

Example 6

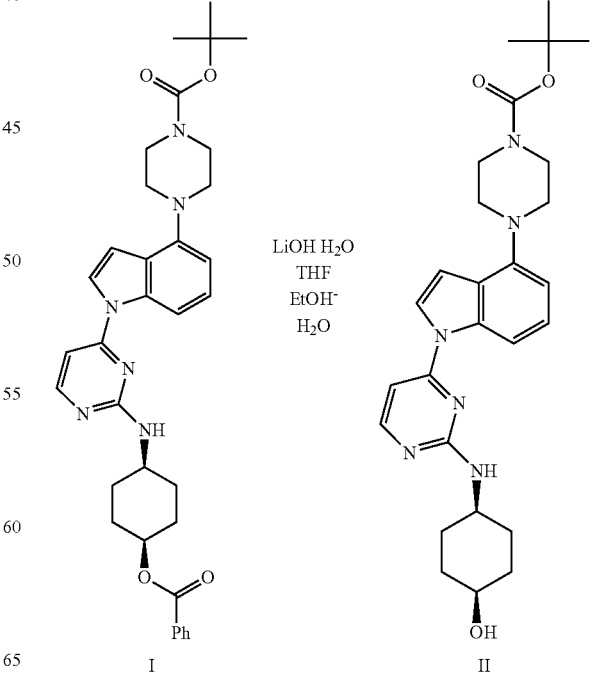

0.225 g of I in 25 mL THF, 5 mL EtOH, and 5 mL H$_2$O was treated with 80 mg of LiOH.H$_2$O and was allowed to stir a r.t. for 2 days. The reaction was then concentrated and allowed to stir until reaction completion. The mixture was then diluted with 1N NaOH, extracted with EtOAc, the organic layer separated and dried over Na$_2$SO$_4$, filtered and concentrated in vacuo to yield 0.165 g II.

Example 7

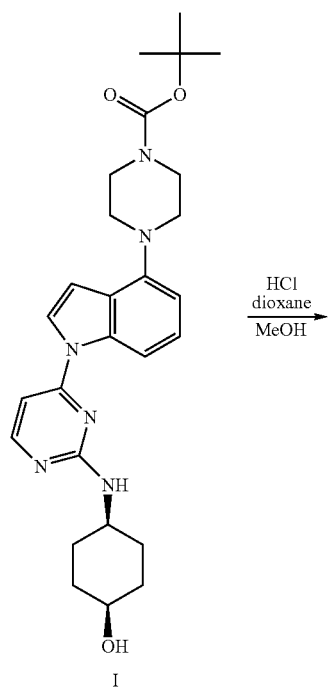

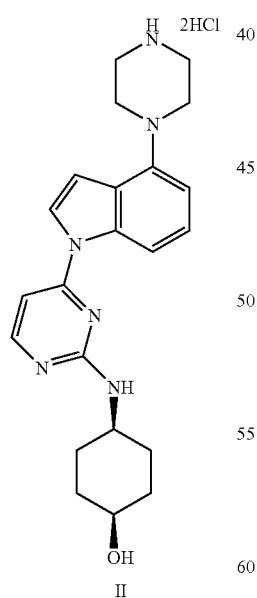

0.165 g of I in 5 mL MeOH was treated with 25 mL 4.0M HCl in dioxane and allowed to stir at r.t. for 4 h and then concentrated in vacuo. The resulting solid was then separated, filtered, and dried in vacuo overnight to yield 0.17 g of II.

Example 8

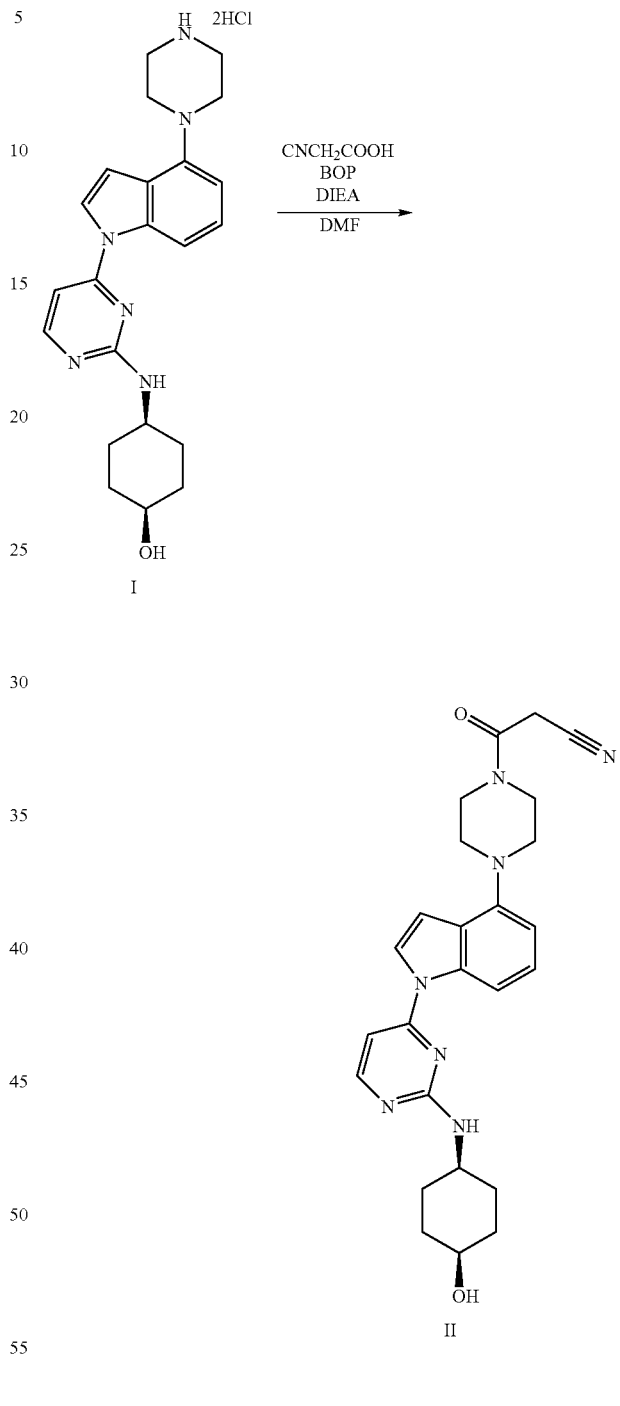

0.1 g of I in 3 mL DMF was treated with 22 mg of CNCH$_2$COOH, 0.12 g BOP, and 0.2 mL DIEA and allowed to stir at r.t. overnight. The mixture was then diluted with water, extracted with DCM, purified on a silica gel column using 100% DCM to 10:1 MeOH:DCM. The fractions containing the product were concentrated in vacuo, the residue triturated with EtOAc, the solid separated, filtered, and dried at 50° C. in vacuo overnight to yield 27.7 mg of II.

Example 9

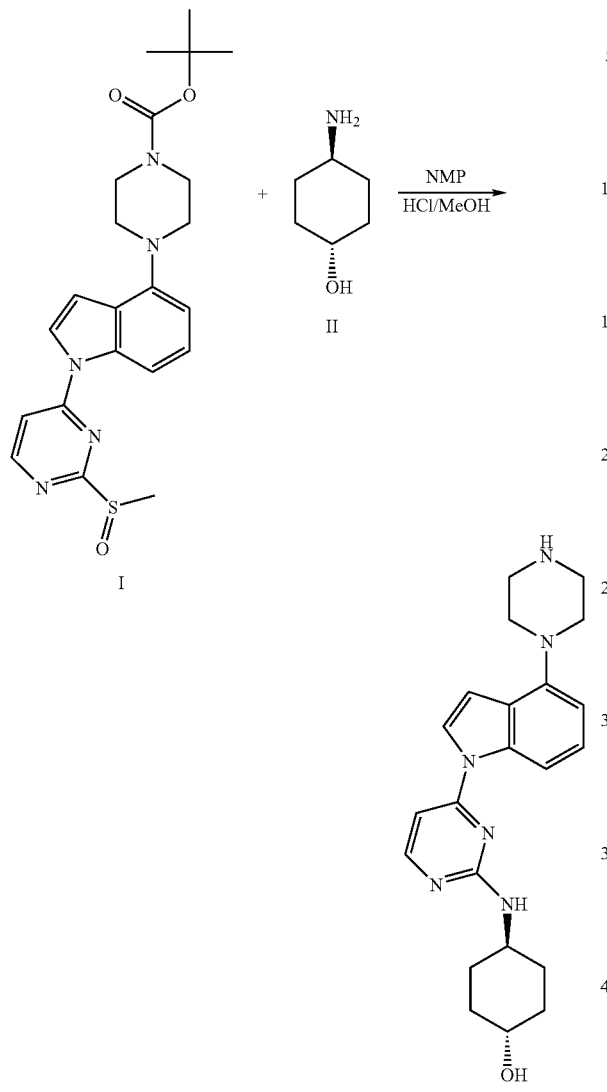

0.3 g of I was treated with 0.235 g of II in 2 mL NMP and stirred at 100° C. for 7 h, cooled to r.t. and diluted with water, the solid separated, filtered, and dried. The solid was then purified by silica gel column using 100% DCM to 10% MeOH/DCM. The fractions containing the product was then concentrated in vacuo overnight, the residue then dissolved in 50 mL HCl/MeOH and stirred at r.t. overnight, then concentrated in vacuo overnight to yield 0.3 g III.

Example 10

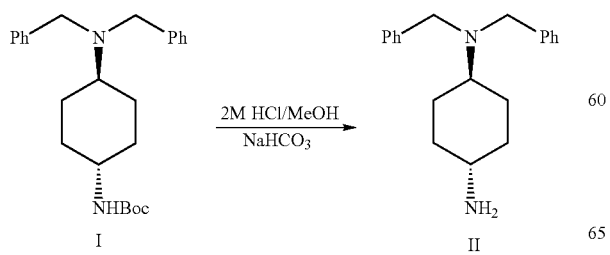

12 g of I in 100 mL 2M HCl/MeOH was allowed to stir at r.t., the mixture concentrated in vacuo, then diluted with water and neutralized with saturated NaHCO₃. the solid was then separated, filtered, and washed with water and dried in vacuo to yield 7 g of II.

Example 11

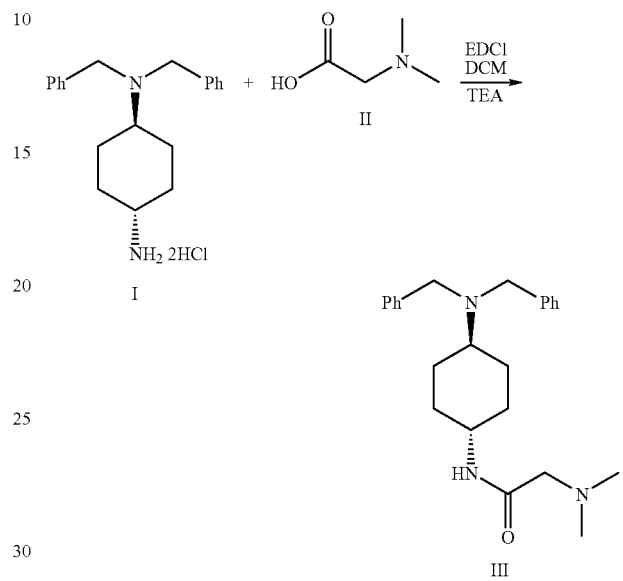

0.776 g of Ii in 100 mL DCM was treated with 1.44 g EDCI, and 2.8 mL TEA and then treated with 1.84 g of I and stirred at r.t. for 4 h. the reaction mixture was then concentrated in vacuo and diluted with water, extracted with DCM, washed with saturated NaHCO₃ and brine, the purified on a silica gel column using 100% DCM to 10% MeOH/DCM. The fractions containing the product were then combined and dried in vacuo to yield 0.61 g of III.

Example 12

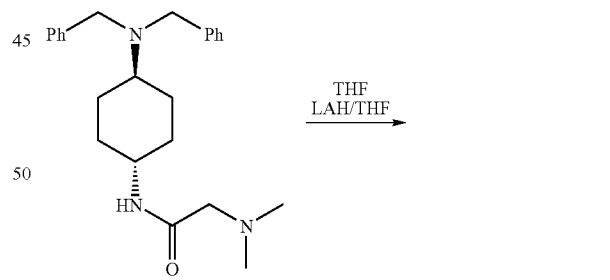

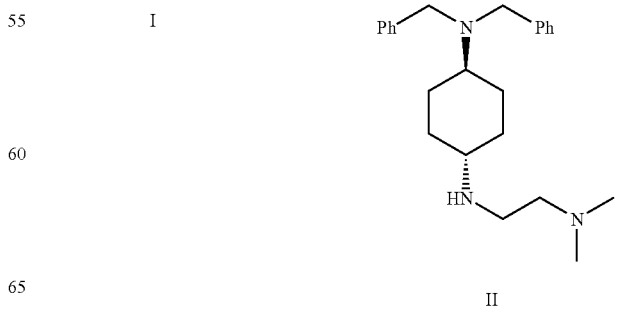

2.2 g of I in 100 mL THF was treated with LAH in THF dropwise at r.t. and refluxed overnight and then cooled to r.t. and quenched with 10% aqueous salt solution, extracted with EtOAc, dried over Na₂SO₄, filtered, and concentrated in vacuo overnight to yield 2.2 g of II.

Example 13

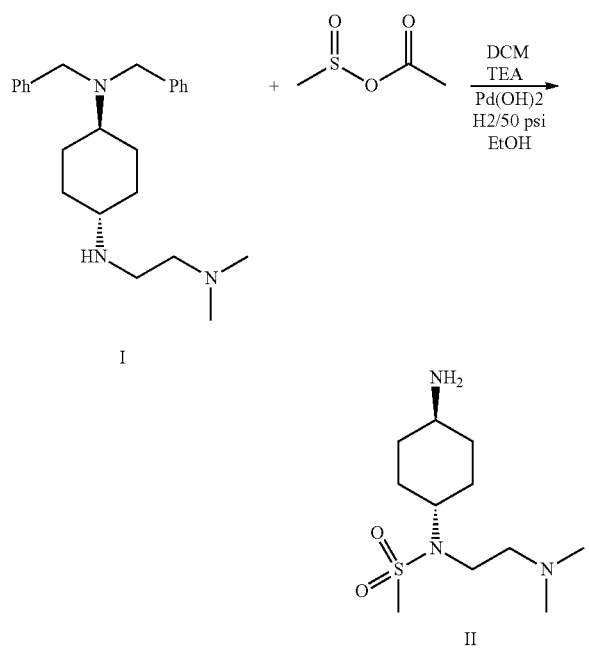

2.2 g of I was treated with 1.15 g of II in 100 mL DCM and treated with 1.7 mL TEA. The product of this reaction was then treated with 0.6 g Pd(OH)₂ and H₂ at 50 psi in 100 mL EtOH to yield 1 g of III.

Example 14

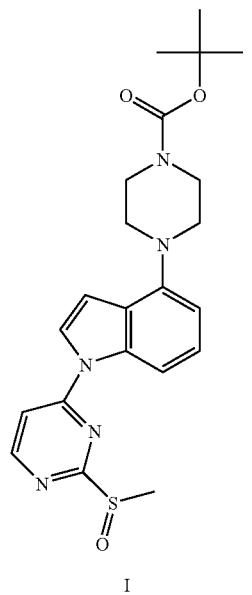

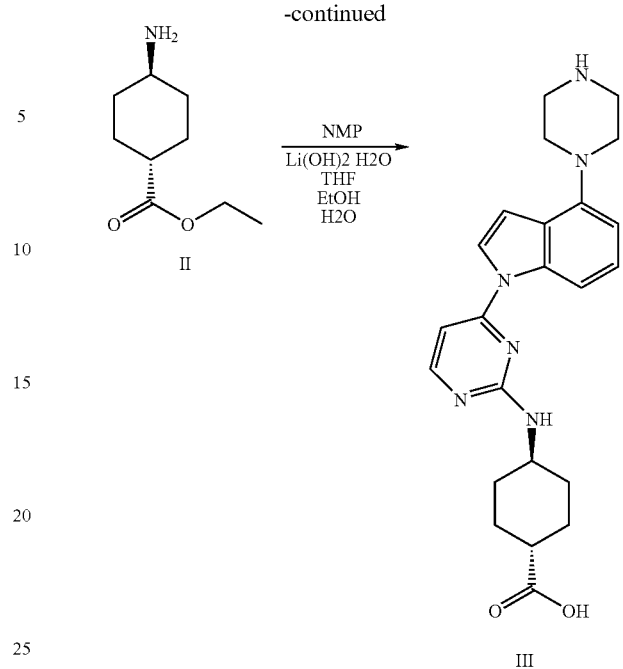

0.4 g of I was treated with 0.465 g of II in 3 mL NMP and stirred at 100° C. for 5 h, cooled to r.t. and diluted with water, the solid separated, filtered, and dried. The solid was then purified by silica gel column using 100% DCM to 5% MeOH/DCM. The fractions containing the product was then concentrated in vacuo overnight, the residue triturated with EtOAc, and the solid separated, filtered, and dried in vacuo. The solid, 028 g, was then dissolved in 20 mL THF and 5 mL EtOH and 0.11 g of Li(OH)₂.H₂O was then added followed by the addition of 5 mL water. The mixture was allowed to stir at r.t. overnight, then concentrated in vacuo then neutralized with HCl and the solid separated, filtered and dried in vacuo overnight at 50° C. to yield 0.244 g III.

Example 15

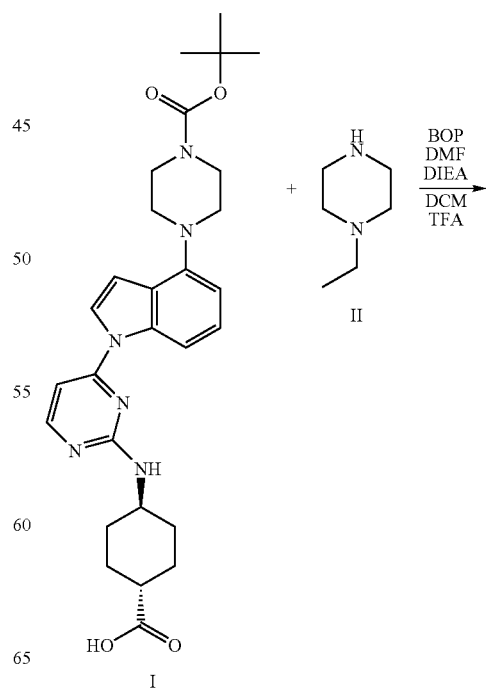

67

-continued

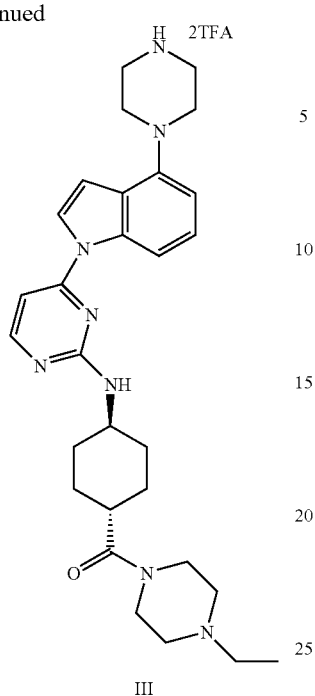

III 0.224 g of I in 2 mL DMF was treated with 0.311 g of BOP, 0.33 mL DIEA, and 80 mg of II and allowed to stir at r.t. overnight, diluted with water, the solid separated, filtered, and then dried in vacuo and purified by silica gel column using 100% DCM to 20% MeOH/DCM and the fractions concentrated in vacuo. The product of this reaction, 0.28 g, was then treated with 3 mL TFA in 30 mL DCM and allowed to stir at r.t. overnight and the solid separated, filtered, dried in vacuo to yield 0.4 g III.

Example 16

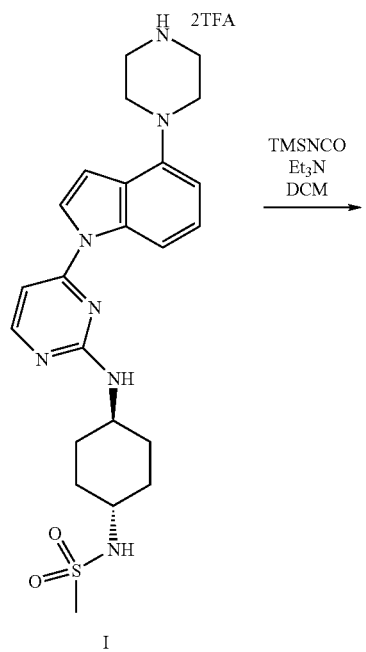

68

-continued

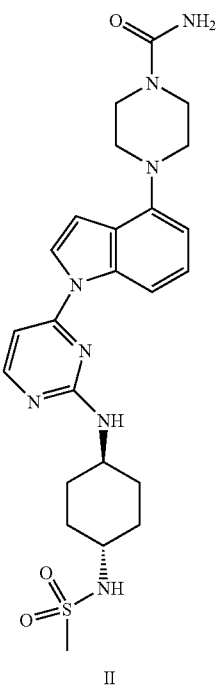

II 0.5 g of I in 3 mL DCM and 3 mL NMP was treated with 0.27 mL Et$_3$N and stirred for 10 min then cooled to 4 C and 0.10 mL TMSNCO then added dropwise and the mixture allowed to warm to r.t. and stirred at r.t. for 18 h and an additional 0.05 mL of TMSNCO added and the mixture allowed to reflux for 2 h and stir at r.t. for 18 h. The mixture was then concentrated in vacuo, water added to precipitate, the solid filtered and purified on a silica gel column using 0% to 5% MeOH/DCM and the fractions dried in vacuo to yield 0.053 g (11%) of product II.

Example 17

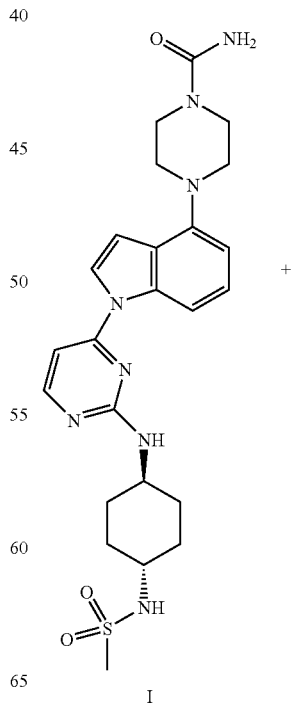

I

Example 18

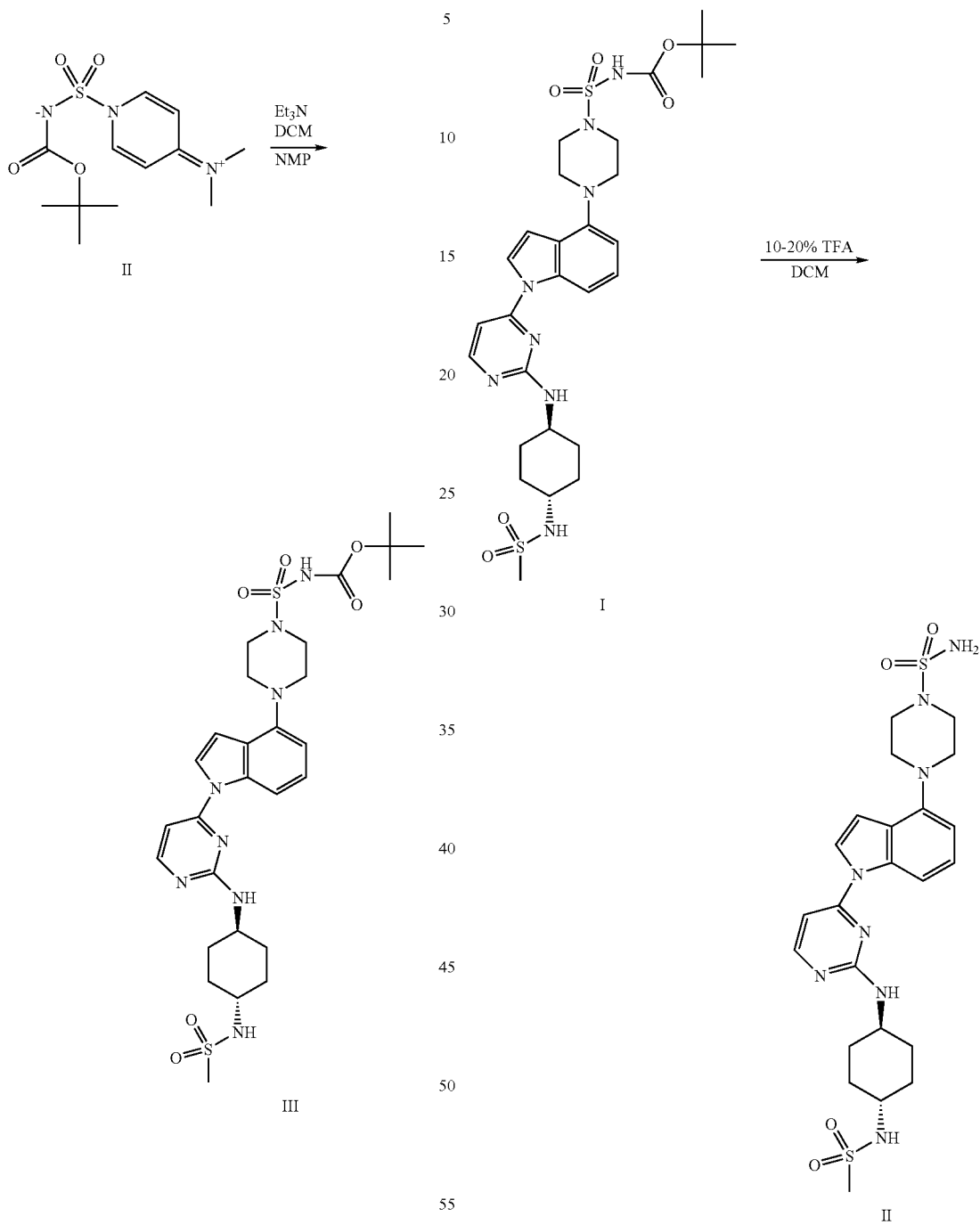

0.5 g of I in 3 mL DCM was treated with 0.27 mL Et3N in 1-3 mL NMP and stirred at r.t. for 10 min and 0.323 g of II then added and the reaction allowed to stir at r.t. for 16 h. The reaction mixture was then diluted with 100 mL EtOAc, washed with water, extracted with EtOAc, the organics combined and washed with water and brine (2×), and dried over $Na_2SO_4$, filtered, and the filtrate concentrated in vacuo, the solid triturated with DCM and pet. Ether, the solid filtered off, and dried in vacuo to yield 0.388 g of III.

0.388 g of I in 20 mL DCM was cooled to 4° C. and treated with 2 mL TFA in 10 mL DCM (20%) and the mixture was allowed to stir at r.t. for 24 h. The reaction mixture was then concentrated in vacuo, extracted with EtOAc, washed with sat'd $NaHCO_3$, the organics dried over $Na_2SO_4$, concentrated and purified on a silica gel column using 0% to 10% MeOH/DCM, and the product triturated with EtOAc and dried in vacuo to yield 0.017 g of II.

Example 19

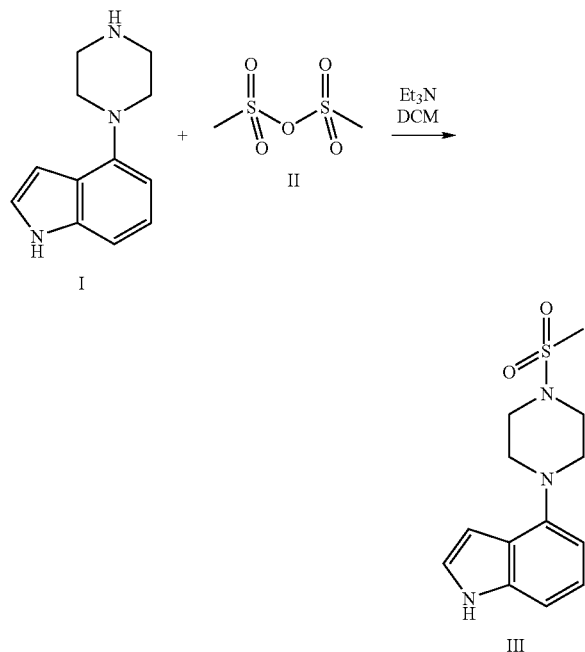

1.0 mL of Et₃N and 0.667 g of II were added to a suspension of I (1.00 g) in 15 mL DCM under N₂. The suspension was cooled on an ice bath to 4° C. and 0.53 mL of Et₃N was added slowly and the reaction allowed to reach r.t., water added, the mixture extracted with DCM and washed with water. The organic layer was dried with Na₂SO₄, concentrated in vacuo to yield the product III (0.950 g, 95%)

Trans-4-{4-[4-(4-Methanesulfonyl-piperidin-1-yl)-indol-1-yl]-pyrimidin-2-ylamino}-cyclohexanol

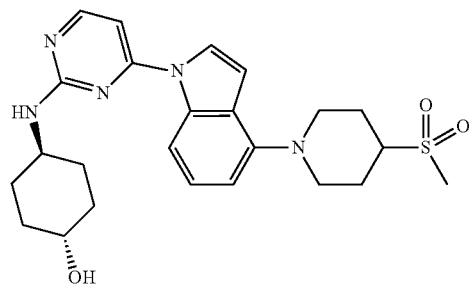 [SMILES: CS(=O)(=O)C1CCN(c2cccc3c2ccn3-c2ccnc(N[C@H]3CC[C@H](O)CC3)n2)CC1]

Step 1: Preparation of 4-bromo-1-(2-methylsulfanyl-pyrimidin-4-yl)-1H-indole

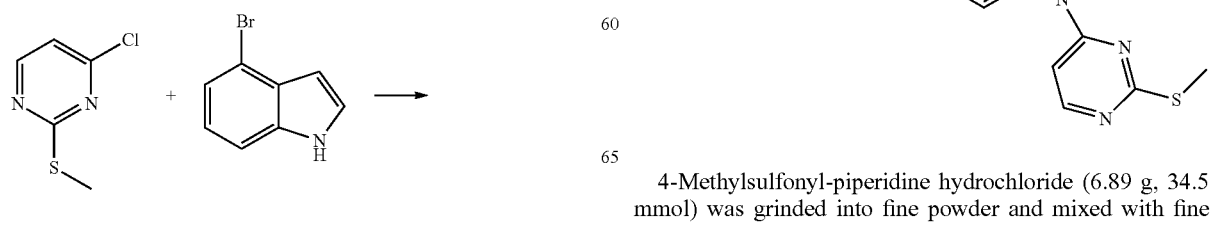

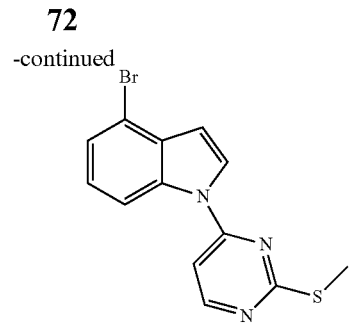

4-Bromoindole (20 g, 102 mmol) was dissolved in 70 mL of NMP and the solution was stirred under ice bath. Sodium hydride (6 g, 60% in mineral oil, 150 mmol) was added in small portions over 30 minutes. The mixture was stirred at room temperature for 40 minutes and then cooled under ice bath. A solution of 4-chloro-2-methylsulfanylpyridine (19.7 g, 122 mmol) in 10 mL of NMP was added through a dropping funnel over 10 minutes. The mixture was stirred at room temperature overnight. Water (150 mL) was added with stirring. The solid material was filtered and washed with water, air dried. This material was suspended in hot ethyl acetate (200 mL) and dichloromethane (200 mL) was added to give a clear solution. Charcoal (5 g) was added and the mixture was stirred for 10 minutes, filtered through Celite. The resulting solution was gently evaporated to remove dichloromethane until crystalline material appeared. The mixture was kept at room temperature for 2 hrs and crystals were filtered, rinsed with cold ethyl acetate (90 mL), air dried, to give 4-bromo-1-(2-methylsulfanyl-pyrimidin-4-yl)-1H-indole as an off white solid (21.5 g, 65%). LC-MS calcd for C₁₃H₁₀BrN₃S (m/e) 318.98, obsd 320.0 (M+H).

Step 2: Preparation of 4-(4-methanesulfonyl-piperidin-1-yl)-1-(2-methylsulfanyl-pyrimidin-4-yl)-1H-indole

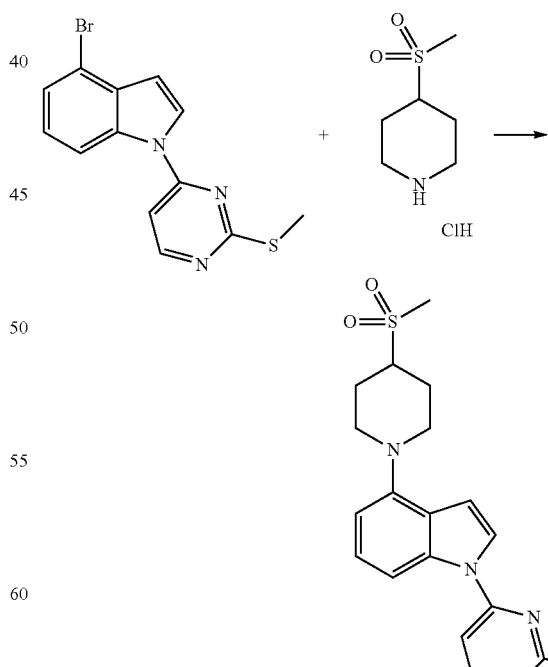

4-Methylsulfonyl-piperidine hydrochloride (6.89 g, 34.5 mmol) was grinded into fine powder and mixed with fine powder of sodium tert-butoxide (7.65 g, 79.6 mmol) in dry dioxane (180 mL). After 30 minutes of stirring, 4-bromo-1-(2-(methylthio)pyrimidin-4-yl)-1H-indole (8.5 g, 26.5 mmol) was added followed by dry dioxane (10 mL) and the mixture was bubbled with argon for 10 minutes. Bis(tri-tert-butylphosphine)palladium (1.02 g, 2.0 mmol) was added followed by dry dioxane (10 mL). The mixture was bubbled with argon for 5 minutes and then sealed. The sealed thick wall bottle was put into oil bath at 65° C. and heated to 120° C. The mixture was stirred at 120° C. for 1.5 hr. The resulting mixture was cooled to 50° C. and filtered through a thin layer of Celite, rinsed with dioxane (100 mL). The filtrate was concentrated and extracted with dichloromethane and saturated ammonium chloride solution. The organic layer was dried and concentrated to a volume about 25 mL. The mixture was treated with ethyl acetate (150 mL) and the yellow solid was filtered to give the desired compound (4.65 g). The filtrate was concentrated and dissolved in dichloromethane and purified through ISCO flash column chromatography (200 g silica gel, 20% to 100% ethyl acetate in hexanes) to give second batch of desired product as a yellow solid (1.67 g, combined total 6.32 g, yield 59.1%). LC-MS calcd for $C_{19}H_{22}N_4O_2S_2$ (m/e) 402.12, obsd 402.9 (M+H).

Example 20

Step 3: Preparation of trans-4-{4-[4-(4-methanesulfonyl-piperidin-1-yl)-indol-1-yl]-pyrimidin-2-ylamino}-cyclohexanol

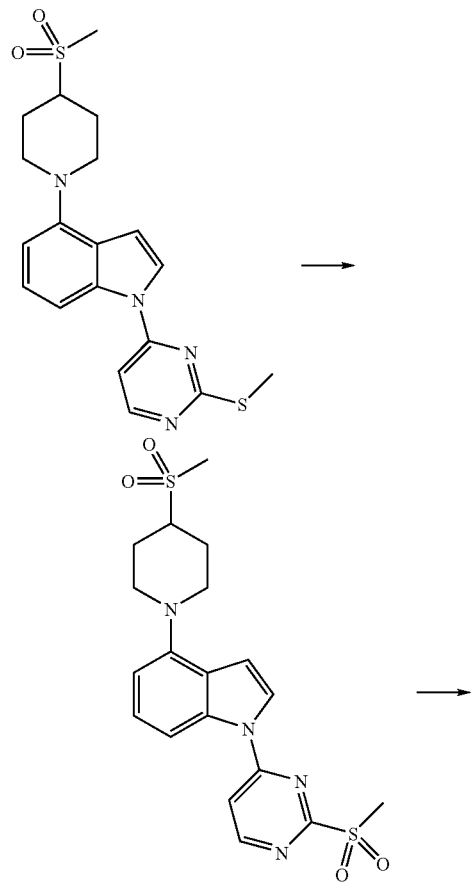

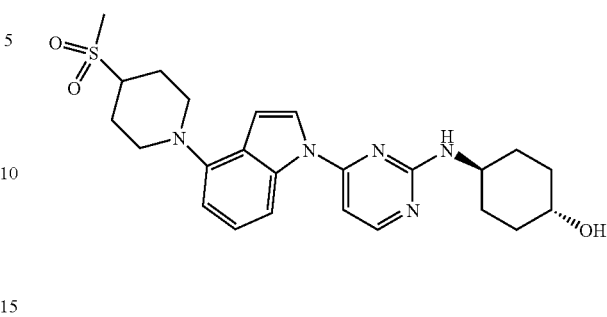

4-(4-(Methylsulfonyl)piperidin-1-yl)-1-(2-(methylthio)pyrimidin-4-yl)-1H-indole (8.02 g, 19.9 mmol) was dissolved in 900 mL of dichloromethane. The solution was cooled under ice bath and MCPBA (15.1 g, max purity 77%, 67 mmol) was added in small portions over 20 minutes with stirring. The mixture was stirred in ice bath for 1 hr and at room temperature for 2 hrs. Stirring bar was removed and the solution was cooled in ice bath. Polymer bound triphenylphosphine (32 g, 3 mmol/g loading, about 96 mmol) was added and the mixture was put on an Orbital Shaker for 12 hrs. The mixture was filtered and rinsed with dichloromethane (400 mL). The filtrate was extracted with 0.2N sodium hydroxide solution (800 mL) and dichloromethane. The organic layer was washed with sodium chloride solution, dried over sodium sulfate and filtered. Solvents were evaporated to give a dark foam material (8.5 g). This material was dissolved in dichloromethane (100 mL) and treated with charcoal (3 g). The resulting mixture was filtered through Celite. The filtrate was treated with hot ethyl acetate (200 mL) and the mixture was gently evaporated to remove dichloromethane. The crystalline material was filtered to give a mixture of sulfone and sulfoxide (1:1 ratio, 4.30 g, 49.7% yield). LC-MS for the sulfone calcd for $C_{19}H_{22}N_4O_4S_2$ (m/e) 434.11, obsd 434.9 (M+H); for the sulfoxide calcd for $C_{19}H_{22}N_4O_3S_2$ (m/e) 418.11, obsd 418.9 (M+H).

The mixed sulfone and sulfoxide from above (4.30 g, 9.9 mmol) and trans-4-aminocyclohexanol (3.42 g, 29.7 mmol) were suspended in 150 mL of dioxane in a sealed tube and stirred at 150° C. for 2 hrs. The mixture was cooled to 40° C. with stirring. The top clear solution was decanted and the dark tar was rinsed with dioxane (60 mL). The combined dioxane solution was evaporated and the residue was extracted with a mixture of ethyl acetate and THF and ammonium chloride solution. The organic layer was washed with concentrated ammonium chloride solution and dried over sodium sulfate. Solvents were evaporated and the residue was dissolved in methanol (200 mL). The clear solution was gently evaporated until crystalline material appeared (less than 20 mL methanol was evaporated). The crystalline mixture was kept at room temperature for 2 hrs and then filtered, rinsed with methanol followed by ether, to give the desired off white crystalline solid as trans-4-{4-[4-(4-methanesulfonyl-piperidin-1-yl)-indol-1-yl]-pyrimidin-2-ylamino}-cyclohexanol (3.27 g, 70.4% yield).

Trans-4-{4-[4-(4-Methanesulfonyl-piperidin-1-yl)-indazol-1-yl]-pyrimidin-2-ylamino}-cyclohexanol

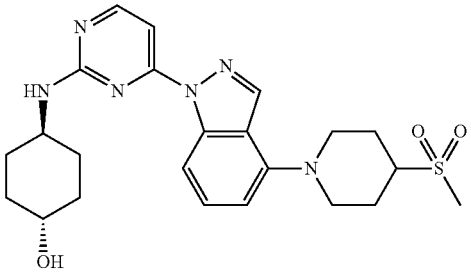 [SMILES: CS(=O)(=O)C1CCN(c2cccc3c2cnn3-c2ccnc(N[C@H]3CC[C@H](O)CC3)n2)CC1]

Step 1: Preparation of N-(2-methylsulfanyl-pyrimidin-4-yl)-hydrazine

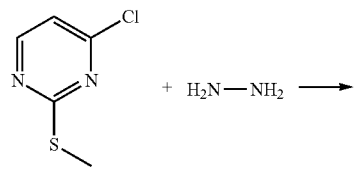

In a 250 mL round bottom flask, 4-chloro-2-methylsulfanyl-pyrimidine (5 g, 31.1 mmol), hydrazine (4.5 g, 140 mmol) and potassium carbonate (6.45 g, 46.7 mmol) were combined with ethanol (50 mL). The mixture was refluxed for 3 hrs and filtered. The filtered solid was rinsed with ethanol (30 mL). The combined ethanol solution was evaporated to give a crude oily mixture which was purified by ISCO flash column chromatography (30% to 100% ethyl acetate in hexanes) to give N-(2-methylsulfanyl-pyrimidin-4-yl)-hydrazine as a white solid (2.8 g, 57.6% yield).

Step 2: Preparation of 2-fluoro-6-(4-methanesulfonylpiperidine-1-yl)benzaldehyde

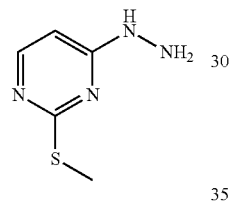

In a 250 mL round bottom flask, 2,6-difluorobenzaldehyde (7.12 g, 5.4 mL, 50.1 mmol), 4-methanesulfonylpiperidine hydrochloride (10 g, 50.1 mmol) and DIPEA (7.77 g, 60.1 mmol) were combined with acetonitrile (75 mL). The mixture was stirred and heated at 80° C. overnight. The mixture was evaporated and extracted with dichloromethane and citric acid solution. The organic layer was washed with brine, dried over sodium sulfate, and evaporated. The crude solid was triturated with cold ethyl acetate to afford 2-fluoro-6-(4-methanesulfonylpiperidine-1-yl)benzaldehyde (12 g, 84% yield). LC-MS calcd for $C_{13}H_{16}FNO_3S$ (m/e) 285.08, obsd 286.0 (M+H).

Step 3: Preparation of 4-(4-methanesulfonyl-piperidin-1-yl)-1-(2-methylsulfanyl-pyrimidin-4-yl)-1H-indazole

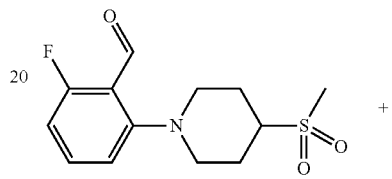

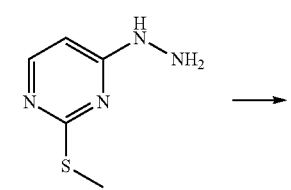

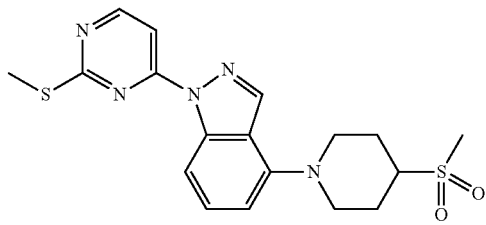

In a 50 ml, round bottom flask, 2-fluoro-6-(4-methanesulfonylpiperidine-1-yl)benzaldehyde (1.37 g, 4.8 mmol), N-(2-methylsulfanyl-pyrimidin-4-yl)-hydrazine (0.75 g, 4.8 mmol) and DBU (2.19 g, 14.4 mmol) were combined with DMSO (17 mL). The mixture was stirred at 180° C. for 1.5 hr in a microwave. The brown solution was blown to dryness and the residue was purified through ISCO flash column chromatography (30% to 100% ethyl acetate in hexanes) to provide 4-(4-methanesulfonyl-piperidin-1-yl)-1-(2-methylsulfanyl-pyrimidin-4-yl)-1H-indazole as a pale orange solid (750 mg, 38.7% yield). LC-MS calcd for $C_{18}H_{21}N_5O_2S_2$ (m/e) 403.11, obsd 404.0 (M+H).

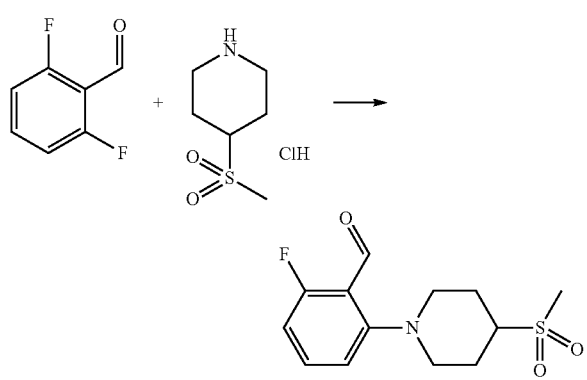

Example 21

Step 4: Preparation of trans-4-{4-[4-(4-methanesulfonyl-piperidin-1-yl)-indazol-1-yl]-pyrimidin-2-ylamino}-cyclohexanol

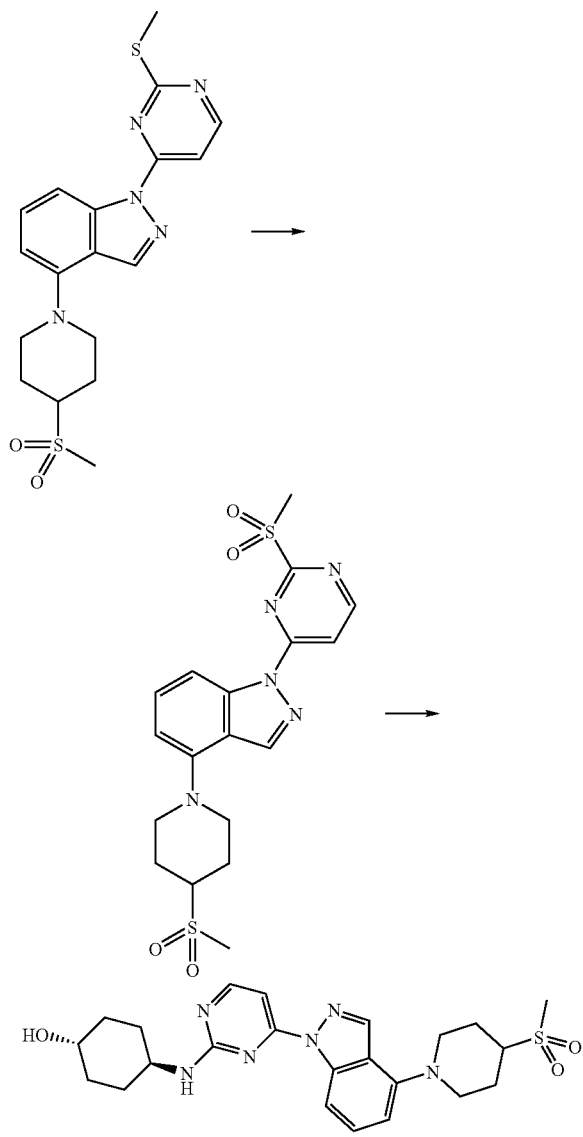

To a 250 mL round bottom flask was added 4-(4-methanesulfonyl-piperidin-1-yl)-1-(2-methylsulfanyl-pyrimidin-4-yl)-1H-indazole (1.1 g, 2.72 mmol) in dichloromethane (75 mL). The solution was stirred under ice bath and MCPBA (1.85 g, 77% maximum, 8.25 mmol) was added in portions. The mixture was stirred under ice bath for 1 hr and then at room temperature for 1.5 hr. The resulting mixture was cooled under ice bath and polymer bound triphenylphosphine (5.0 g, 3 mmol/g loading) was added. The mixture was put on an Orbital Shaker for 12 hrs and then filtered, rinsed with dichloromethane (75 mL). The filtrate was extracted with 0.2N sodium hydroxide solution and dichloromethane. The organic layer was washed with sodium chloride solution, dried over sodium sulfate and filtered. Solvents were evaporated to give a yellow solid material (1.36 g). LC-MS indicated 70% sulfone and 30% sulfoxide. LC-MS for the sulfoxide calcd for $C_{18}H_{21}N_5O_3S_2$ (m/e) 419.11, obsd 420.0 (M+H); LC-MS for the sulfone calcd for $C_{18}H_{21}N_5O_4S_2$ (m/e) 435.10, obsd 436.0 (M+H).

The above yellow solid compound (1.36 g) was mixed with trans-4-aminocyclohexanol (950 mg, 8.25 mmol) in a sealed thick wall bottle containing dioxane (100 mL). The mixture was stirred in an oil bath heated to 120° C. After 7 hrs of heating, the mixture was cooled down and extracted with a mixture of THF (20 mL), ethyl acetate (60 mL) and saturated ammonium chloride solution (50 mL). The aqueous phase was further extracted with ethyl acetate (100 mL). The combined organic layer was dried over sodium sulfate and filtered. Solvents were evaporated and the residue was purified through ISCO flash column chromatography (40 g silica gel, 5% to 10% acetic acid in ethyl acetate) to provide trans-4-{4-[4-(4-methanesulfonyl-piperidin-1-yl)-indazol-1-yl]-pyrimidin-2-ylamino}-cyclohexanol as a pale yellow solid (490 mg, 38.2% yield, two steps). LC-MS calcd for $C_{23}H_{30}N_6O_3S$ (m/e) 470.21, obsd 471.0 (M+H).

Biological Assays
JNK Assay in vitro

JNK activity was measured by phosphorylation of GST-ATF2 (19-96) with [γ-$^{33}$P] ATP. The enzyme reaction was conducted at Km concentrations of ATP and the substrate at final volume of 40 µl in buffer containing 25 mM HEPES, pH 7.5, 2 mM dithiothreitol, 150 mM NaCl, 20 mM $MgCl_2$, 0.001% Tween® 20, 0.1% BSA and 10% DMSO. Human JNK2α2 assay contains 1 nM enzyme, 1 µM ATF2, 8 µM ATP with 1 uCi [γ-$^{33}$P] ATP. Human JNK1α1 assay contains 2 nM enzyme, 1 µM ATF2, 6 µM ATP with 1 µCi [γ-$^{33}$P] ATP. Human JNK3 (Upstate Biotech #14-501M) assay contains 2 nM enzyme, 1 µM ATF2, 4 µM ATP with 1 µCi [γ-$^{33}$P] ATP. The enzyme assay was carried out in the presence or absence of several compound concentrations. JNK and compound were pre-incubated for 10 min., followed by initiation of the enzymatic reaction by adding ATP and the substrate. The reaction mixture was incubated at 30° C. for 30 min. At the end of incubation, the reaction was terminated by transferring 25 µl of the reaction mixture to 150 µl of 10% glutathione Sepharose® slurry (Amersham #27-4574-01) containing 135 mM EDTA. The reaction product was captured on the affinity resin, and washed on a filtration plate (Millipore, MAB-VNOB50) with phosphate buffered saline for six times to remove free radionucleotide. The incorporation of $^{33}$P into ATF2 was quantified on a microplate scintillation counter (Packard Topcount). Compound inhibition potency on JNK was measured by $IC_{50}$ value generated from ten concentration inhibition curves fitted into the 3-parameter model: % inhibition=Maximum/$(1+(IC_{50}/[Inhibitor])^{slope})$. Data were analyzed on Microsoft Excel for parameter estimation. Representative results are shown in Table 1 below:

TABLE 1

Representative Compound $IC_{50}$'s for JNK1 and JNK2

| Compound | JNK1 (µM) | JNK2 (µM) |
|---|---|---|
| I-1 | 0.211 | 1.4296 |
| I-2 | 0.0939 | 0.6544 |
| I-3 | 0.0293 | 0.182 |
| I-4 | 0.0429 | 0.292 |
| I-5 | 0.0103 | 0.1054 |
| I-6 | 0.003 | 0.0235 |
| I-7 | 0.0191 | 0.0861 |
| I-8 | 0.014 | 0.0823 |
| I-9 | 0.0054 | 0.0362 |
| I-10 | 0.0104 | 0.0749 |
| I-11 | 0.01 | 0.0681 |

TABLE 1-continued

Representative Compound IC$_{50}$'s for JNK1 and JNK2

| Compound | JNK1 (µM) | JNK2 (µM) |
|---|---|---|
| I-12 | 0.0031 | 0.0179 |
| I-13 | 0.0066 | 0.0493 |
| I-14 | 0.003 | 0.0192 |
| I-15 | 0.0036 | 0.0208 |
| I-16 | 0.0117 | 0.066 |
| I-17 | 0.0085 | 0.0477 |
| I-18 | 0.0083 | 0.0332 |
| I-19 | 0.0061 | 0.0328 |
| I-20 | 0.0068 | 0.0401 |
| I-21 | 0.0312 | 0.1376 |
| I-22 | 0.0036 | 0.0264 |
| I-23 | 0.3775 | 1.6251 |
| I-24 | 0.0777 | 0.477 |
| I-25 | 0.0042 | 0.0256 |
| I-26 | 0.0037 | 0.0246 |
| I-27 | 0.002 | 0.0128 |
| I-28 |  | 0.0555 |
| I-29 |  | 0.525 |
| I-30 |  | 0.0827 |
| I-31 | 0.0096 | 0.0548 |
| I-32 | 0.0124 | 0.0856 |
| I-33 |  | 0.1978 |
| I-34 |  | 0.0892 |
| I-35 |  | 0.1768 |
| I-36 |  | 0.1678 |
| I-37 | 0.0484 | 4.026 |
| I-38 | 0.0049 | 0.0428 |
| I-39 |  | 0.4055 |
| I-40 |  | 0.035 |
| I-41 | 0.025 | 0.1638 |
| I-42 | 0.0024 | 0.0136 |
| I-43 |  | 0.4318 |
| I-44 |  | 0.0192 |
| I-45 |  | 0.0334 |
| I-46 |  | 0.036 |
| I-47 |  | 0.0296 |
| I-48 |  | 0.0545 |
| I-49 |  | 0.0598 |
| I-50 |  | 0.0156 |
| I-51 | 0.0036 | 0.0062 |
| I-52 |  | 0.0218 |
| I-53 |  | 0.0117 |
| I-54 |  | 0.0152 |
| I-55 | 0.0044 | 0.0231 |
| I-56 | 0.0092 | 0.0187 |
| I-57 | 0.0159 | 0.0884 |
| I-58 |  | 0.806 |
| I-59 |  | 0.5702 |
| I-60 |  | 0.1497 |
| I-61 |  | 0.1054 |
| I-62 | 0.0321 | 0.1452 |
| I-63 | 0.0124 | 0.0257 |
| I-64 |  | 0.0139 |
| I-65 |  | 0.0268 |
| I-66 | 0.0058 | 0.0167 |

Rat in vivo TNFα-Induced IL-6 Production Assay:

Female Wistar-Han rats procured from Charles River Laboratories are allowed to acclimate for one week prior to use and achieve an approximate body weight of 101-130 g. Rats are administered test compound (N=8 per compound) via oral gavage 30 min prior to an intraperitoneal challenge of 0.5 µg recombinant rat TNF-α (Biosource). Blood is collected via cardiocentesis 90 min after TNF-α challenge. Plasma is prepared using lithium heparin separation tubes (BD microtainer) and frozen at −80° C. until analyzed. IL-6 levels are determined using a rat specific IL-6 ELISA kit (Biosource). The percent inhibition and ED$_{50}$ values (calculated as the dose of compound at which TNF-α production is 50% of the control value) are determined.

Rat in vivo TNFα-Induced IL-6 Production Assay:

Female Wistar-Han rats procured from Charles River Laboratories are allowed to acclimate for one week prior to use and achieve an approximate body weight of 114-132 g. Rats are administered compound 18 (N=8 per dose) subcutaneously 30 min prior to an intra-peritoneal challenge of 0.5 µg recombinant rat TNF-α (Biosource). Blood is collected via cardiocentesis 90 min after TNF-α challenge. Plasma is prepared using lithium heparin separation tubes (BD microtainer) and frozen at −80° C. until analyzed. IL-6 levels are determined using a rat specific IL-6 ELISA kit (Biosource). The percent inhibition and ED$_{50}$ values (calculated as the dose of compound at which TNF-α production is 50% of the control value) are determined.

Rodent Collagen-induced Arthritis:

Female Lewis rats procured from Harlan Laboratories at 7-8 weeks of age are allowed to acclimate for one week prior to use and achieve an approximate body weight of 120-140 g. On day 0 of study, rats are primed intradermally (i.d.) on several sites on the back with an emulsion of 100 µg Bovine Type II Collagen (Chondrex) in Incomplete Freund's adjuvant (IFA; total of 0.1 ml in 2-3 sites). Arthritis induction is generally observed 12-14 days from priming; however a booster injection of 100 µg collagen/IFA is given around days 7-10 (i.d. up to 0.1 ml total) at the base of the tail or an alternate site on back to synchronize disease induction. Compound dosing can be prophylactic (starting at time of boost or 1-2 days prior) or therapeutic (beginning after boost and coinciding with initial disease scores of 1-2—see clinical scoring below). Animals are evaluated for the development and progression of disease over the next 21 days.

Rats are evaluated using a scoring system (described below), paw volume measurements using a plethysmometer for each paw, or measuring paw or joint thickness with a caliper. Base-line measurements are performed on day 0, and starting again at the first signs of swelling for up to three times per week until the end of the experiment. Scoring is evaluated as follows for each paw:

1=swelling and/or redness of paw or one digit.
2=swelling in two or more joints.
3=gross swelling of the paw with more than two joints involved.
4=severe arthritis of the entire paw and digits.

The arthritic index for each rat is evaluated by adding the four scores of the individual paws, giving a maximum score of 16. In order to serially measure disease onset and progression, the paw volume of the hind paws is also determined through the use of a plethysmometer.

At the end of the study, the hind paws (and other tissues) are harvested for weight determination, histology, cellular and/or molecular analysis. Additionally, blood is collected via cardiocentesis, plasma is prepared using lithium heparin separation tubes (BD microtainer) and frozen at −70° C. until analyzed. Inflammatory cytokine levels (e.g., TNF-α, IL-1 and IL-6) from the plasma or from homogenized joint tissue are determined using rat-specific ELISA kits (R&D). The level of disease protection or inhibition is determined as a composite of changes in clinical scores, paw volumes and histopathology compared to control animals.

Rat Pharmacokinetic Study:

Female Wistar/Han (CRL: WI) Rats (Charles River, Hollister, Calif.) weighing between 180 and 220 g are used. Animals are allowed free access to a standard laboratory chow and tap water and are housed in a constant temperature-humidity environment. Three rats per dose regime are administered either single 10 mg/kg IV bolus doses (50% cyclodextran/water) or single 10 mg/kg oral suspension doses prepared in aqueous vehicle containing 0.9% NaCl, 0.5% sodium carboxymethyl cellulose, 0.4% polysorbate 80 and 0.9% benzyl alcohol. Blood is collected from each rat anesthetized with $CO_2:O_2$ (60:40) via the orbital sinus or cardiac puncture at 1, 3, 6, 8, and 24 h after dosing. Plasma levels of test compounds are assayed by a LC/MS method. In this method, an aliquot of plasma is treated by mixing with acetonitrile to precipitate protein, centrifuged to clarify the supernatant, then further diluted with formate buffer (50 mM), and injected onto an HPLC. Test compounds are separated from endogenous interfering substances and subsequently eluted from the HPLC column for mass spectrometric quantification.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:
1. A compound of formula I

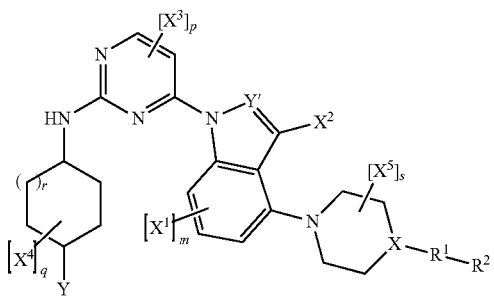

or a pharmaceutically acceptable salt thereof,
wherein:
Y' is CH or N;
X is CH or N;
each $X^1$ is independently halogen, lower alkyl, lower alkoxy, lower haloalkyl, or hydroxy;
m is 0, 1, or 2;
$X^2$ is H, lower alkyl, lower alkoxy, amido, lower haloalkyl, or lower haloalkoxy;
$X^3$ is lower alkyl, lower alkoxy, or lower haloalkyl;
p is 0 or 1;
each $X^4$ is independently lower alkyl, lower alkoxy, lower haloalkyl, hydroxy, lower hydroxylalkyl, $OC(=O)Z^2$, or halogen;
$X^5$ is lower alkyl;
s is 0, 1, or 2;
q is 0, 1, or 2;
r is 0 or 1;
Y is H, OH, $C(=O)Z^2$, $C(=O)OZ^2$, $OZ^2$, $OC(=O)Z^2$, $N(Z^1)C(=O)(Z^2)$, $C(Z^1)_2S(O)_2Z^2$, $N(Z^1)S(O)_2Z^2$, $N(Z^1)S(O)_2N(Z^1)(Z^2)$, $C(Z^1)_2(Z^2)$, or $(C=O)N(Z^1)(Z^2)$;
$Z^1$ is H or $Z^{1'}$;
$Z^{1'}$ is lower alkyl, optionally substituted with one or more $Z''$;
each $Z''$ is independently halogen, hydroxy, lower haloalkyl, dialkylamino or amino;
$Z^2$ is H or $Z^{2'}$;

$Z^{2'}$ is hydroxy, lower alkyl, lower alkoxy, lower hydroxyalkyl, lower haloalkyl, cycloalkyl, cycloalkyl lower alkyl, heterocycloalkyl, heterocycloalkyl lower alkyl, optionally substituted with one or more $Z^{2''}$;
each $Z^{2''}$ is independently halogen, hydroxy, lower alkyl, cycloalkyl, cyano, lower haloalkyl, amino, carboxylic acid, ester, or lower alkoxy;
$R^1$ is a bond, $C(=O)$, $C(=O)O$, $C(=O)CH_2OC(=O)$, $C(=O)CH_2NHC(=O)O$, or $S(=O)_2$;
$R^2$ is H or $R^{2'}$;
$R^{2'}$ is hydroxy, lower alkyl, $N(R^3)_2$, lower hydroxyalkyl, or lower haloalkyl, optionally substituted with one or more $R^{2''}$;
each $R^{2''}$ is independently cyano, amino, dialkylamino, hydroxy, lower hydroxyalkyl, or lower alkoxy; and
each $R^3$ is independently H, lower alkyl, lower cycloalkyl, phenyl, lower heterocycloalkyl, or both $R^3$ together form a heterocyclic ring;
with the proviso that when X is N, $X^2$ is H, Y' is CH, $R^1$ is $C(=O)$, $R^2$ is methyl, r is 1, m is 0, p is 0, q is 0, Y is $N(Z^1)S(O)_2Z^2$, and $Z^2$ is methyl, then $Z^1$ is not H or hydroxyethyl.

2. The compound of claim 1, wherein m is 0, $X^2$ is H, p is 0, q is 0, r is 0, X is N, Y' is CH, $R^1$ is $C(=O)$, $R^2$ is $R^{2'}$, $R^{2'}$ is methylene, and $R^{2''}$ is cyano.

3. The compound of claim 1, wherein m is 0, p is 0, q is 0, r is 1, X is N, Y' is CH, $R^1$ is $C(=O)$, $R^2$ is $R^{2'}$, $R^{2'}$ is methylene, and $R^{2''}$ is cyano.

4. The compound of claim 1, wherein m is 0, $X^2$ is H, p is 0, q is 0, r is 1, X is N, Y' is CH, $R^1$ is $C(=O)$, $R^2$ is $R^{2'}$, and $R^{2'}$ is methyl.

5. The compound of claim 1, wherein m is 0, p is 0, q is 0, r is 1, X is CH, Y' is CH, $R^1$ is $S(=O)_2$, $R^2$ is $R^{2'}$, and $R^{2'}$ is methyl.

6. The compound of claim 1, wherein $R^1$ is $C(=O)$, $R^2$ is $R^{2'}$, $R^{2'}$ is methylene, and $R^{2''}$ is cyano.

7. The compound of claim 1, wherein $R^1$ is $S(=O)_2$, $R^2$ is $R^{2'}$, and $R^{2'}$ is methyl.

8. A compound selected from the group consisting of:
N-{4-[4-(4-Piperazin-1-yl-indol-1-yl)-pyrimidin-2-ylamino]-cyclohexyl}-methanesulfonamide;
4-[4-(4-Piperidin-1-yl-indol-1-yl)-pyrimidin-2-ylamino]-cyclohexanol;
N-(4-{4-[4-(4-Methanesulfonyl-piperazin-1-yl)-indol-1-yl]-pyrimidin-2-ylamino}-cyclohexyl)-methanesulfonamide;
N-(4-{4-[4-(4-Hydroxy-piperidin-1-yl)-indol-1-yl]-pyrimidin-2-ylamino}-cyclohexyl)-methanesulfonamide;
N-(4-{4-[4-(4-Acetyl-piperazin-1-yl)-indol-1-yl]-pyrimidin-2-ylamino}-cyclohexyl)-N-methyl-methanesulfonamide;
N-(4-{4-[4-(4-Methanesulfonyl-piperidin-1-yl)-indol-1-yl]-pyrimidin-2-ylamino}-cyclohexyl)-methanesulfonamide;
4-{1-[2-(4-Methanesulfonylamino-cyclohexylamino)-pyrimidin-4-yl]-1H-indol-4-yl}-piperazine-1-carboxylic acid amide;
4-{1-[2-(4-Methanesulfonylamino-cyclohexylamino)-pyrimidin-4-yl]-1H-indol-4-yl}-piperazine-1-sulfonic acid amide;
N-[4-(4-{4-[4-(2-Cyano-acetyl)-piperazin-1-yl]-indol-1-yl}-pyrimidin-2-ylamino)-cyclohexyl]-methanesulfonamide;

Acetic acid 2-(4-{1-[2-(4-methanesulfonylamino-cyclohexylamino)-pyrimidin-4-yl]-1H-indol-4-yl}-piperazin-1-yl)-2-oxo-ethyl ester;
N-[4-(4-{4-[4-(2-Hydroxy-acetyl)-piperazin-1-yl]-indol-1-yl}-pyrimidin-2-ylamino)-cyclohexyl]-methanesulfonamide;
4-{4-[4-(4-Methanesulfonyl-piperidin-1-yl)-indol-1-yl]-pyrimidin-2-ylamino}-cyclohexanol;
N-(4-{4-[4-(4-Methanesulfonyl-piperidin-1-yl)-indol-1-yl]-pyrimidin-2-ylamino}-cyclohexyl)-acetamide;
2-(4-{4-[4-(4-Methanesulfonyl-piperidin-1-yl)-indol-1-yl]-pyrimidin-2-ylamino}-cyclohexyl)-propan-2-ol;
[4-{4-[4-(4-Methanesulfonyl-piperidin-1-yl)-indol-1-yl]-pyrimidin-2-ylamino}-cyclohexyl]aminodimethylsulfonamide;
4-{4-[4-(4-Methanesulfonyl-piperidin-1-yl)-indol-1-yl]-pyrimidin-2-ylamino}-1-methyl-cyclohexanol;
4-{4-[4-(4-Methanesulfonyl-piperidin-1-yl)-indol-1-yl]-pyrimidin-2-ylamino}-1-methyl-cyclohexanol;
(4-Hydroxy-piperidin-1-yl)-(4-{4-[4-(4-methanesulfonyl-piperidin-1-yl)-indol-1-yl]-pyrimidin-2-ylamino}-cyclohexyl)-methanone;
4-{4-[4-(4-Methanesulfonyl-piperidin-1-yl)-indol-1-yl]-pyrimidin-2-ylamino}-cyclohexanecarboxylic acid ethylamide;
4-{4-[4-(4-Methanesulfonyl-piperidin-1-yl)-indol-1-yl]-pyrimidin-2-ylamino}-cyclohexanecarboxylic acid ethyl ester;
1-[(R)-4-(1-{2-[4-(4-Hydroxy-piperidine-1-carbonyl)-cyclohexylamino]-pyrimidin-4-yl}-1H-indol-4-yl)-3-methyl-piperazin-1-yl]-ethanone;
[2-(4-{1-[2-(4-Methanesulfonylamino-cyclohexylamino)-pyrimidin-4-yl]-1H-indol-4-yl}-piperazin-1-yl)-2-oxo-ethyl]-carbamic acid tent-butyl ester;
N-[4-(4-{4-[4-(2-Dimethylamino-acetyl)-piperazin-1-yl]-indol-1-yl}-pyrimidin-2-ylamino)-cyclohexyl]-methanesulfonamide;
N-[4-(4-{4-[4-(2-Amino-acetyl)-piperazin-1-yl]-indol-1-yl}-pyrimidin-2-ylamino)-cyclohexyl]-methanesulfonamide;
3-[4-(1-{2-[4-((R)-3-Hydroxy-pyrrolidin-1-ylmethyl)-cyclohexylamino]-pyrimidin-4-yl}-1-1H-indol-4-yl)-piperazin-1-yl]-3-oxo-propionitrile;
N-[4-(4-{4-[4-(2-Cyano-acetyl)-piperazin-1-yl]-indol-1-yl}-pyrimidin-2-ylamino)-cyclohexyl]-N-(2-dimethylamino-ethyl)-methanesulfonamide;
3-(4-{1-[2-(4-Hydroxymethyl-cyclohexylamino)-pyrimidin-4-yl]-1H-indol4-yl}-piperazin-1-yl)-3-oxo-propionitrile;
3-[4-(1-{2-[4-((S)-3-Hydroxy-pyrrolidin-1-ylmethyl)-cyclohexylamino]-pyrimidin-4-yl}-1H-indol-4-yl)-piperazin-1-yl]-3-oxo-propionitrile;
1-[4-(1-{2-[4-((R)-3-Hydroxy-pyrrolidin-1-ylmethyl)-cyclohexylamino]-pyrimidin-4-y1}-1H-indol-4-yl)-piperazin-1-yl]-ethanone;
(4-Ethoxy-piperidin-1-yl)-(4-{4-[4-(4-methanesulfonyl-piperidin-1-yl)-indol-1-yl]-pyrimidin-2-ylamino}-cyclohexyl)-methanone;
((R)-3-Ethoxy-pyrrolidin-1-yl)-(4-{4-[4-(4-methanesulfonyl-piperidin-1-yl)-indol-1-yl]-pyrimidin-2-ylamino}-cyclohexyl)-methanone;
((S)-3-Ethoxy-pyrrolidin-1-yl)-(4-{4-[4-(4-methanesulfonyl-piperidin-1-yl)-indol-1-yl]-pyrimidin-2-ylamino}-cyclohexyl)-methanone;
Cyano-acetic acid (1R,3S)-3-(4-{4-[4-(2-cyano-acetyl)-piperazin-1-yl]-indol-1-yl}-pyrimidin-2-ylamino)-cyclohexyl ester;
3-(4-{1-[2-((1S,3S)-3-Hydroxy-cyclohexylamino)-pyrimidin-4-yl]-1H-indol-4-yl}-piperazin-1-yl)-3-oxo-propionitrile;
3-(4-{1-[2-((1S,3R)-3-Hydroxy-cyclohexylamino)-pyrimidin-4-yl]-1H-indol-4-yl}-piperazin-1-yl)-3-oxo-propionitrile;
Cyano-acetic acid (1S,3S)-3-(4-{4-[4-(2-cyano-acetyl)-piperazin-1-yl]-indol-1-yl}-pyrimidin-2-ylamino)-cyclohexyl ester;
1-{4-[1-(2-Cyclohexylamino-pyrimidin-4-yl)-1H-indol-4-yl]-piperazin-1-yl}-ethanone;
3-{4-[1-(2-Cyclohexylamino-pyrimidin-4-yl)-1H-indol-4-yl]-piperazin-1-yl}-3-oxo-propionitrile;
1-[4-(1-{2-[4-(2-Methoxy-ethoxy)-cyclohexylamino]-pyrimidin-4-yl}-1H-indol-4-yl)-piperazin-1-yl]-ethanone;
3-[4-(1-{2-[4-(2-Methoxy-ethoxy)-cyclohexylamino]-pyrimidin-4-yl}-1H-indol-4-yl)-piperazin-1-yl]-3-oxo-propionitrile;
1-(4-{1-[2-(4-Methanesulfonylmethyl-cyclohexylamino)-pyrimidin-4-yl]-1H-indol-4-yl}-piperazin-1-yl)-ethanone;
3-(4-{1-[2-(4-Methanesulfonylmethyl-cyclohexylamino)-pyrimidin-4-yl]-1H-indol-4-yl}-piperazin-1-yl)-3-oxo-propionitrile;
1-[4-(1-{2-[4-(1-Hydroxy-1-methyl-ethyl)-cyclohexylamino]-pyrimidin-4-yl}-1H-indol-4-yl)-piperazin-1-yl]-ethanone;
N-[4-(4-{4-[4-(2-Cyano-acetyl)-piperazin-1-yl]-indol-1-yl}-pyrimidin-2-ylamino)-cyclohexyl]-N-(2-hydroxy-ethyl)-methanesulfonamide;
3-[4-(1-{2-[4-(1-Hydroxy-1-methyl-ethyl)-cyclohexylamino]-pyrimidin-4-yl}-1H-indol-4-yl)-piperazin-1-yl]-3-oxo-propionitrile;
(4-Ethyl-piperazin-1-yl)-(4-{4-[4-(4-methanesulfonyl-piperidin-1-yl)-indol-1-yl]-pyrimidin-2-ylamino}-cyclohexyl)-methanone;
(4-Cyclopropyl-piperazin-1-yl)-(4-{4-[4-(4-methanesulfonyl-piperidin-1-yl)-indol-1-yl]-pyrimidin-2-ylamino}-cyclohexyl)-methanone;
(4-tert-Butyl-piperazin-1-yl)-(4-{4-[4-(4-methanesulfonyl-piperidin-1-yl)-indol-1-yl]-pyrimidin-2-ylamino}-cyclohexyl)-methanone;
(4-Cyclobutyl-piperazin-1-yl)-(4-{4-[4-(4-methanesulfonyl-piperidin-1-yl)-indol-1-yl]-pyrimidin2-ylamino}-cyclohexyl)-methanone;
(4-{4-[4-(4-Methanesulfonyl-piperidin-1-yl)-indol-1-yl]-pyrimidin-2-ylamino}-cyclohexyl)-(octahydro-pyrido[1,2-α]pyrazin-2-yl)-methanone;
(4-{4-[4-(4-Methanesulfonyl-piperidin-1-yl)-indol-1-yl]-pyrimidin-2-ylamino}-cyclohexyl)-(3-trifluoromethyl-5,6-dihydro-8H-[1,2,4]triazolo[4,3-α]pyrazin-7-yl)-methanone;
(Hexahydro-pyrrolo[1,2-α]pyrazin-2-yl)-(4-{4-[4-(4-methanesulfonyl-piperidin-1-yl)-indol-1-yl]-pyrimidin-2-ylamino}-cyclohexyl)-methanone;
(5,6-Dihydro-8H-[1,2,4]triazolo[4,3-α]pyrazin-7-yl)-(4-{4-[4-(4-methanesulfonyl-piperidin-1-yl)-indol-1-yl]-pyrimidin-2-ylamino}-cyclohexyl)-methanone;
(5,6-Dihydro-8H-imidazo[1,2-α]pyrazin-7-yl)-(4-{4-[4-(4-methanesulfonyl-piperidin-1-yl)-indol-1-yl]-pyrimidin-2-ylamino }-cyclohexyl)-methanone;
3-(4-{1[2-(4-Hydroxy-cyclohexylamino)-pyrimidin-4-yl]-1H-indol-4-yl}-piperazin-1-yl)-3-oxo-propionitrile;

3-[4-(1-{2-[4-(4-Ethyl-piperazine-1-carbonyl)-cyclohexylamino]-pyrimidin-4-yl}-1H-indol-4-yl)-piperazin-1-yl]-3-oxo-propionitrile;

3-(4-{1-[2-(4-Hydroxy-cyclohexylamino)-pyrimidin-4-yl]-1H-indol-4-yl}-piperazin-1-yl)-3-oxo-propionitrile;

3-(4-{1-[2-((1S,3R)-3-Hydroxy-cyclopentylamino)-pyrimidin-4-yl]-1H-indol-4-yl}-piperazin-1-yl)-3-oxo-propionitrile;

3-(4-{1-[2-((1R,3S)-3-Hydroxy-cyclopentylamino)-pyrimidin-4-yl]-1H-indol-4-yl}-piperazin-1-yl)-3-oxo-propionitrile;

3-(4-{1-[2-((1S,3S)-3-Hydroxy-cyclopentylamino)-pyrimidin-4-yl]-1H-indol-4-yl}-piperazin-1-yl)-3-oxo-propionitrile;

3-(4-{1-[2-((1R,3R)-3-Hydroxy-cyclopentylamino)-pyrimidin-4-yl]-1H-indol-4-yl}-piperazin-1-yl)-3-oxo-propionitrile;

4-{4-[4-(4-Methanesulfonyl-piperidin-1-yl)-indol-1-yl]-pyrimidin-2-ylamino}-cyclohexanol;

4-(4-Acetyl-piperazin-1-yl)-1-[2-(4-hydroxy-cyclohexylamino)-pyrimidin-4-yl]-1H-indole-3-carboxylic acid amide;

4-(4-Acetyl-piperazin-1-yl)-1-[2-(4-methanesulfonylmethyl-cyclohexylamino)-pyrimidin-4-yl]-1H-indole-3-carboxylic acid amide;

4-{4-[4-(4-Methanesulfonyl-piperidin-1-yl)-indazol-1-yl]-pyrimidin-2-ylamino}-cyclohexanecarboxylic acid ethyl ester; and 4-{4-[4-(4-Methanesulfonyl-piperidin-1-yl)-indazol-1-yl]-pyrimidin-2-ylamino}-cyclohexanol.

9. A method of treating rheumatoid arthritis comprising administering to a subject in need thereof a therapeutically effective amount of the compound of claim 1, wherein the treatment is palliative.

10. A method of treating asthma comprising administering to a subject in need thereof a therapeutically effective amount of the compound of claim 1, wherein the treatment is palliative.

11. A method of treating type II diabetes comprising administering to a subject in need thereof a therapeutically effective amount of the compound of claim 1, wherein the treatment is palliative.

12. A pharmaceutical composition comprising the compound of claim 1, admixed with at least one pharmaceutically acceptable carrier, excipient or diluent.

13. A method for treating arthritis comprising co-administering to a patient in need thereof a therapeutically effective amount of an anti-inflammatory compound in combination with the compound of claim 1, wherein the treatment is palliative.

14. A method of treating arthritis comprising administering to a subject in need thereof a therapeutically effective amount of the compound of claim 1, wherein the treatment is palliative.

* * * * *